US010851046B2

(12) United States Patent
Wang et al.

(10) Patent No.: US 10,851,046 B2
(45) Date of Patent: Dec. 1, 2020

(54) VEGETABLE OIL-BASED MATERIAL AS A SUBSTITUTE FOR CARNAUBA WAX

(71) Applicant: Iowa State University Research Foundation, Inc., Ames, IA (US)

(72) Inventors: Tong Wang, Ames, IA (US); Tao Fei, Ames, IA (US)

(73) Assignee: IOWA STATE UNIVERSITY RESEARCH FOUNDATION, INC., Ames, IA (US)

(*) Notice: Subject to any disclaimer, the term of this patent is extended or adjusted under 35 U.S.C. 154(b) by 0 days.

(21) Appl. No.: 15/926,203

(22) Filed: Mar. 20, 2018

(65) Prior Publication Data

US 2018/0297937 A1 Oct. 18, 2018

Related U.S. Application Data

(60) Provisional application No. 62/474,896, filed on Mar. 22, 2017.

(51) Int. Cl.
*C07C 237/12* (2006.01)
*C11C 3/00* (2006.01)
(Continued)

(52) U.S. Cl.
CPC .......... *C07C 237/12* (2013.01); *C07C 231/02* (2013.01); *C07C 233/40* (2013.01);
(Continued)

(58) Field of Classification Search
CPC .... C07C 237/12; C07C 231/02; C07C 233/40
(Continued)

(56) References Cited

U.S. PATENT DOCUMENTS 2,356,408 A 8/1944 Kelley
8,147,606 B2 4/2012 Heinrichs
(Continued)

FOREIGN PATENT DOCUMENTS

WO WO-2014085576 A1 * 6/2014 ............. A01N 37/46

OTHER PUBLICATIONS

Chem Abstr. of KR 2014/147188 (Year: 2014).*
(Continued)

*Primary Examiner* — Deborah D Carr
(74) *Attorney, Agent, or Firm* — Troutman Pepper Hamilton Sanders LLP

(57) ABSTRACT

This invention relates to a wax composition comprising a plurality of fatty acid amide compounds having the Formula (I):

$$R^1 \underset{H}{\overset{O}{\underset{\|}{N}}} (\text{─})_{n_1} \overset{H}{\underset{O}{\overset{\|}{N}}} [(\text{─})_{n_2}]_{m_1} \overset{H}{\underset{O}{\overset{\|}{N}}} (\text{─})_{n_1} \underset{H}{\overset{O}{\underset{\|}{N}}} R^2$$ (I)

where $R^1$, $R^2$, $n_1$, $n_2$, $m_1$, and $m_2$ are as described herein. This invention also relates to a wax composition comprising:
a) one or more fatty acid amide compounds having the Formula (II):
(Continued)

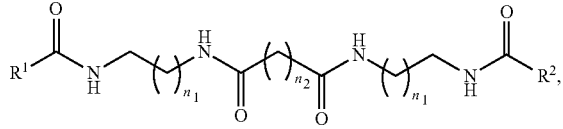

(II)

and
  b) one or more fatty acid amide compounds having the Formula (III):

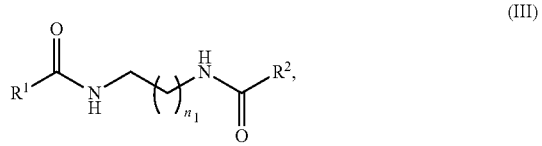

(III)

where $R^1$, $R^2$, $n_1$, and $n_2$ are as described herein. This invention also relates to a fatty acid amide compound having the Formula (I) and a process for preparing a compound of Formula (I).

15 Claims, 8 Drawing Sheets

(51) Int. Cl.
  *C08L 91/06* (2006.01)
  *C07C 231/02* (2006.01)
  *C11C 3/12* (2006.01)
  *C11C 3/04* (2006.01)
  *C07C 233/40* (2006.01)

(52) U.S. Cl.
  CPC ............... *C08L 91/06* (2013.01); *C11C 3/00* (2013.01); *C11C 3/003* (2013.01); *C11C 3/04* (2013.01); *C11C 3/12* (2013.01)

(58) Field of Classification Search
  USPC .......................................................... 554/35
  See application file for complete search history.

(56) References Cited

U.S. PATENT DOCUMENTS

| 2013/0036713 A1* | 2/2013 | Daute ................ B01J 19/0013 53/473 |
| 2013/0156720 A1* | 6/2013 | Currie ................ A61K 31/155 424/78.01 |

OTHER PUBLICATIONS

Computer generated abstract of WO 2014/123775 showing that the registry number of the compound recited in the office action. (Year: 2014).*

CAS abstract of US-20130036713 (computer-generated) which shows the compound recited in the office action called bisamide (Year: 2013).*

Fei et al., "Soybean Oil as Feedstock for the Synthesis and Characterization of a Carnauba Substitute and a Study of the Structure-Function Relationships," Journal of Industrial and Engineering Chemistry 57:416-423 (2018).

Gessner G. Hawley "The Condensed Chemical Dictionary," Tenth Edition, Van Nostrand Reinhold Company p. 132 (1981).

PubChem SID: 319114429.

Brady et al., "Pantocin B, an Antibiotic from Erwinia herbicola Discovered by Heterologous Expression of Cloned Genes," Am. Chem. Soc. 121(50):11912-11913 (1999).

Fei et al., "Developing and Commercializing Vegetable Oil-Based Coating Materials USB #1440-612-06480," Presentation, Dept. of Food Science and Human Nutrition, Center for Crops Utilization Research, Iowa State University 1-23 (Mar. 15-17, 2016).

* cited by examiner

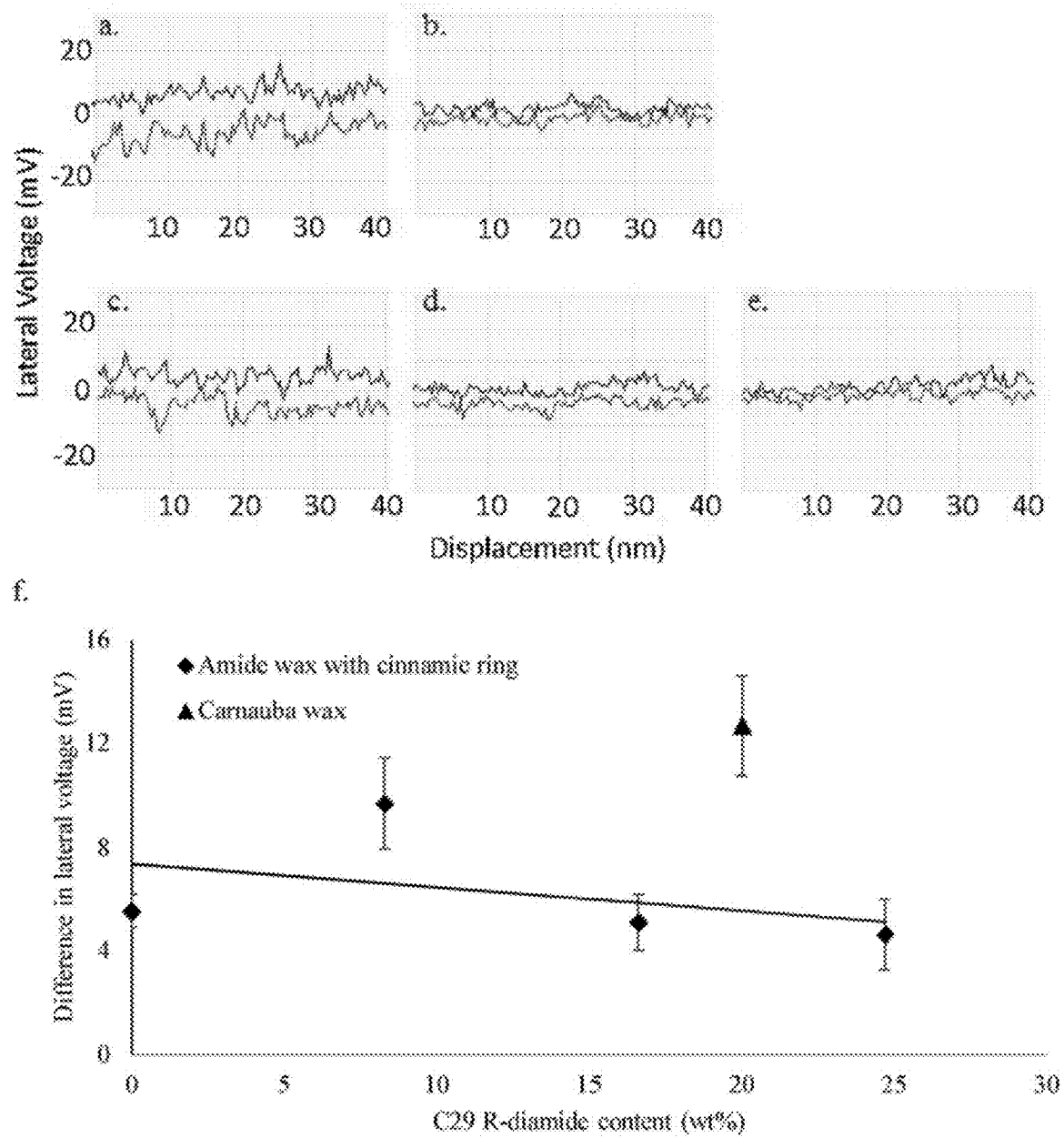
Figures 4A-F

VEGETABLE OIL-BASED MATERIAL AS A SUBSTITUTE FOR CARNAUBA WAX

This application claims the priority benefit of U.S. Provisional Patent Application Ser. No. 62/474,896, filed Mar. 22, 2017, which is hereby incorporated by reference in its entirety.

FIELD OF THE INVENTION

The present invention relates to novel fatty acid amide based wax compositions and methods of making and using thereof.

BACKGROUND OF THE INVENTION

The limited resource for carnauba wax that has high hardness, high melting point (82-86° C.), and desirable surface properties has led researchers to seek alternatives for carnauba wax. Wax derived from vegetable oil has been an interest of innovators because of its relatively abundant supply and low price. With hydrogenated castor oil (HCO) and ethanolamine (ETA), compounds containing hydroxylated saturated fatty acids with alkylolamines and esterified alkylolamine can be produced and used as hard wax substitute as described in (U.S. Pat. No. 2,356,408 to Kelley). Fatty alkanolamides, diamides, and aralkylamides also can be synthesized directly from triglycerides and primary amines at low temperatures (Fealrheller et al., "A Novel Technique for the Preparation of Secondary Fatty Amide," *J. Am. Oil Chem. Soc.* 71:863-866 (1994)). However, the hardness and surface characteristics of the amide/diamide waxes are not as good as carnauba and these properties still need to be improved. Using hydrogenated castor oil is also not economical, and lower-priced renewable raw materials need to be identified. There are few studies on developing vegetable oil based carnauba substitute, and even fewer systematically reported structure-function relationships of the amide/diamide waxes. The effects of different functional groups on physical properties remained relatively unknown.

Carnauba wax is mainly produced by mechanically recovering the coating from the leaves of a variety of palm trees that almost executively grow in northeastern Brazil. The composition of this wax was reported by Vandenburg et al., "The Structural Constituents of Carnauba Wax," *J. Am. Oil Chem. Soc.* 47:514-518 (1970) as follows: hydrocarbon (0.3-1%), aliphatic esters (38-40%), monohydric alcohols (10-12%), ω-hydroxy aliphatic esters (12-14%), p-methoxycinnamic aliphatic diesters (5-7%), p-hydroxycinnamic aliphatic diesters (20-23%), a triterpene type of diol (0.4%), and free fatty acids and other unknown constituents (5-7%). The esters have carbon numbers between 44 and 66 (Basson et al., "An Investigation of the Structures and Molecular Dynamics of Natural Waxes: II Carnauba Wax," *J. Phys. D: Appl. Phys.* 21:1429 (1988)), and the alkanes have carbon numbers between 16 and 34 (Vandenburg et al., "The Structural Constituents of Carnauba Wax," *J. Am. Oil Chem. Soc.* 47:514-518 (1970)). The presence of long chain esters is believed to contribute to the high melting point and hardness of carnauba wax. In addition to the esters, the mixtures of substituted long-chain aliphatic hydrocarbons, containing alkanes, fatty acids, and primary and secondary alcohols also play an important role (Waksmundzka-Hajnos et al., "Phytochemistry, Phytopharmacology, and the Biological Role of Plant Metabolites," *High Performance Liquid Chromatography in Phytochemical Analysis*, Boca Raton, Fla. CRC Press, pp. 89-106, particularly p. 92 (2011)).

It is believed that different functional groups contribute to different physical properties of carnauba wax. Fatty alcohols and ω-hydroxy fatty acids and their esters probably contribute to cohesiveness of the wax. Wang et al., "Chemical Modification of Partially Hydrogenated Vegetable Oil to Improve its Functional Properties," *J. Am. Oil Chem. Soc.* 84:1149-1159 (2007) reported that incorporating hydroxyl groups to hydrogenated soybean oil can improve its cohesiveness, and the study suggested a positive relationship between the quantity of hydroxyl groups and degree of cohesiveness. The aromatic ring structure that cinnamic acid brought to the diesters was believed to be responsible for the desirable surface properties of carnauba wax (Vandenburg et al., "Aromatic Acids of Carnauba Wax," *J. Am. Oil Chem. Soc.* 46:659-662 (1967)).

The present invention is directed to overcoming these and other deficiencies in the art.

SUMMARY OF THE INVENTION

One aspect of the invention relates to a fatty acid amide compound having the Formula (I):

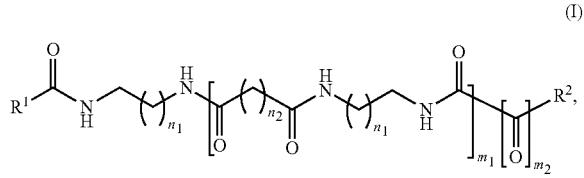

wherein:
R$^1$ a substituted or unsubstituted C$_3$ to C$_{50}$ alkyl or substituted or unsubstituted aryl;
R$^2$ is H, substituted or unsubstituted C$_3$ to C$_{50}$ alkyl, substituted or unsubstituted arylalkyl, substituted or unsubstituted arylalkenyl, or substituted or unsubstituted aryl;
n$_1$ is an integer from 0 to 10;
n$_2$ is an integer from 1 to 20;
m$_1$ is 0 or 1; and
m$_2$ is 0 or 1, and
wherein m$_1$+m$_2$ cannot be 2.

Another aspect of the invention relates to a wax composition comprising a plurality of fatty acid amide compounds having the Formula (I):

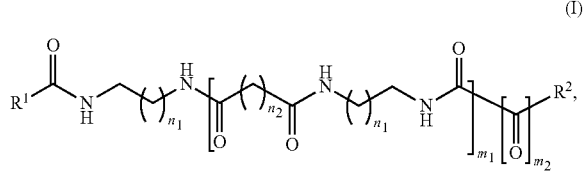

wherein:
R$^1$ a substituted or unsubstituted C$_3$ to C$_{50}$ alkyl or substituted or unsubstituted aryl;
R$^2$ is H, substituted or unsubstituted C$_3$ to C$_{50}$ alkyl, substituted or unsubstituted arylalkyl, substituted or unsubstituted arylalkenyl, or substituted or unsubstituted aryl;

$n_1$ is an integer from 0 to 10;
$n_2$ is an integer from 1 to 20;
$m_1$ is 0 or 1; and
$m_2$ is 0 or 1, and
wherein $m_1+m_2$ cannot be 2.

Another aspect of the invention relates to a wax composition comprising:

a) one or more fatty acid amide compounds having the Formula (II):

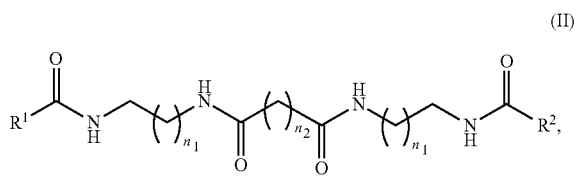

(II)

and b) one or more fatty acid amide compounds having the Formula (III):

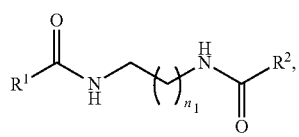

(III)

wherein:
$R^1$ is each independently a substituted or unsubstituted $C_3$ to $C_{50}$ alkyl or substituted or unsubstituted aryl;
$R^2$ is each independently substituted or unsubstituted $C_3$ to $C_{50}$ alkyl, substituted or unsubstituted arylalkyl, substituted or unsubstituted arylalkenyl, or substituted or unsubstituted aryl;
$n_1$ is an integer from 0 to 10; and
$n_2$ is an integer from 1 to 20;
wherein component a) and component b) are blended together.

Another aspect of the invention relates to a process for preparing a compound of Formula (I):

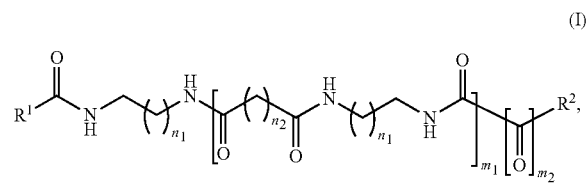

(I)

said process comprising:
providing one or more monoamide compounds having the Formula (IV):

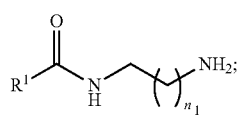

(IV)

providing one or more acids having the Formula (V)

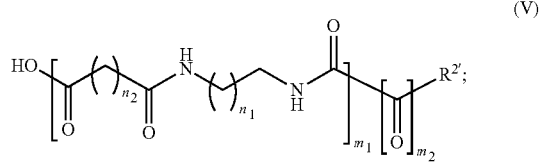

(V)

wherein
$R^1$ is a substituted or unsubstituted $C_3$ to $C_{50}$ alkyl;
$R^{2'}$ is OH, substituted or unsubstituted $C_3$ to $C_{50}$ alkyl, substituted or unsubstituted arylalkyl, substituted or unsubstituted arylalkenyl, or substituted or unsubstituted aryl;
$n_1$ is an integer from 0 to 10;
$n_2$ is an integer from 1 to 20;
$m_1$ is 0 or 1; and
$m_2$ is 0 or 1,
wherein $m_1+m_2$ cannot be 2; and
reacting the one or more monoamide compounds having the Formula (IV) with the one or more acids having Formula (V) under conditions effective to make the compound of Formula (I).

In the present invention, soybean oil-based wax materials with physical properties similar to that of carnauba wax were developed. The soybean oil-based carnauba wax substitute will significantly increase the availability of the high-priced hard wax. A systematic structure-function relationship study was conducted using free fatty acids from fully hydrogenated soybean oil. This study and the resulting established relationship can be used for tailored synthesis of vegetable oil-based wax materials. The inventors of the present application assumed that: 1) an amide bond will achieve high melting and high hardness compared to an ester bond, and terminating the free —NH$_2$ group from the monoamide with a diacid to increase carbon chain length can further significantly increase hardness of the material and 2) introducing proper amount of cinnamic ring to the structure can improve surface shininess and reduce surface friction of the material. In the present invention, different molar ratio of reactants were used and mixtures of monoamide and diamide were synthesized and further reacted with diacids and cinnamic acid. The physical properties of these mixtures were compared, and an optimal soybean oil-based carnauba substitute was identified.

In the present invention, soybean oil-based hard materials useful as a carnauba wax substitute were developed. Structure-function relationships were studied and established. Amide derivatives of the saturated fatty acid were shown to have a higher hardness and melting point than the ester derivative of the same chain length. Using the free amine group on the linear end of a monoamide to react with a diacid further increased chain length and thus hardness, with hardness increasing as the content of polyamide increased. The cinnamic acid ring structure was confirmed as contributing to the shininess and smoothness of carnauba wax, because incorporating this group in fatty acid diamide and incorporating 12.4 wt % of diamide with cinnamic ring structure significantly improved the shininess of the resulting material. However, further increasing the content of cinnamic rings did not further improve shininess and smoothness. Overall, a material principally consisted of 76.3 wt % of polyamide with 52 carbon atoms, 11.3 wt % of short chain diamide with 38 carbon atoms, and 12.4 wt % of diamide with 29 carbon atoms having cinnamic ring attached was shown to have comparable hardness and surface properties as carnauba wax was. Therefore, in the present invention, soybean oil was successfully used as the feedstock to synthesize a high-melting hard wax that may be used as a carnauba wax substitute. This material may have unique applications where high temperature tolerance is needed.

BRIEF DESCRIPTION OF THE DRAWINGS

FIGS. 4A-E are images showing AFM trace-retrace curves of carnauba wax (FIG. 4A); mixture of C52 polyamide (90.0 wt %) and C38 diamide (10.0 wt %) (FIG. 4B); mixture of C52 polyamide (80.8 wt %); C38 diamide (10.9 wt %), and C29 R-diamide (8.3 wt %) (FIG. 4C); (d) mixture of C52 polyamide (71.8 wt %), C38 diamide (11.6 wt %), and C29 R-diamide (16.6 wt %) (FIG. 4D); and (e) mixture of C52 polyamide (62.9 wt %), C38 diamide (12.4 wt %), and C29 R-diamide (24.7 wt %) (FIG. 4E). FIG. 4F is a graph showing the curve of lateral voltage difference between trace and retrace curves of wax samples which is an indicator of the coefficient of friction.

DETAILED DESCRIPTION OF THE INVENTION

Figure 1A:
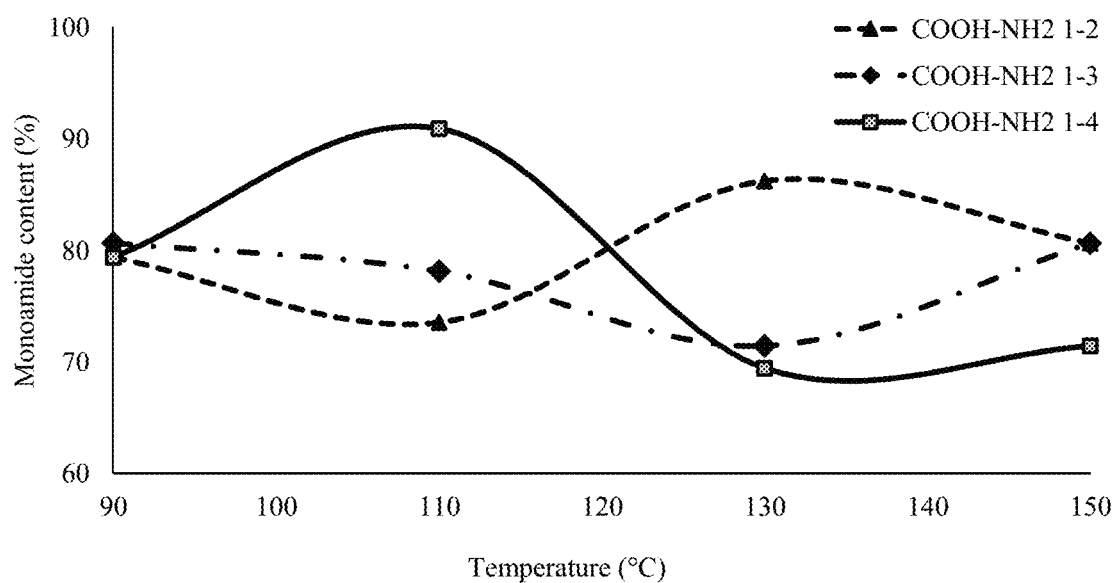
FIGS. 1A-B are graphs showing effect of reactant ratio and temperature on formation of monoamide (FIG. 1A) and effect of monoamide content on hardness of the resulted material (FIG. 1B).

As used above, and throughout the description herein, the following terms, unless otherwise indicated, shall be understood to have the following meanings. If not defined otherwise herein, all technical and scientific terms used herein have the same meaning as is commonly understood by one of ordinary skill in the art to which this technology belongs. In the event that there is a plurality of definitions for a term herein, those in this section prevail unless stated otherwise.

The term "alkyl" means an aliphatic hydrocarbon group which may be straight or branched. When not otherwise restricted, the term refers to an alkyl of 50 or fewer carbons. Branched means that one or more lower alkyl groups such as methyl, ethyl, or propyl are attached to a linear alkyl chain. Exemplary alkyl groups include methyl, ethyl, n-propyl, i-propyl, n-butyl, t-butyl, n-pentyl, 3-pentyl, and the like.

The term "alkenyl" means an aliphatic hydrocarbon group containing a carbon—carbon double bond and which may be straight or branched having about 2 to about 50 carbon atoms in the chain. Branched means that one or more lower alkyl groups such as methyl, ethyl, or propyl are attached to a linear alkenyl chain. Exemplary alkenyl groups include ethenyl, propenyl, n-butenyl, and i-butenyl.

The term "aryl" means an aromatic monocyclic or multi-cyclic (polycyclic) ring system of 6 to about 19 carbon atoms, or of 6 to about 10 carbon atoms. The ring system of the aryl group may be optionally substituted. Representative aryl groups include, but are not limited to, groups such as phenyl, naphthyl, azulenyl, phenanthrenyl, anthracenyl, fluorenyl, pyrenyl, triphenylenyl, chrysenyl, and naphthacenyl.

The term "monocyclic" used herein indicates a molecular structure having one ring.

The term "polycyclic" or "multi-cyclic" used herein indicates a molecular structure having two or more rings, including, but not limited to, fused, bridged, or spiro rings.

The terms "arylalkyl" mean an alkyl substituted with one or more aryl groups, wherein the alkyl and aryl groups are as herein described. One particular example is an arylmethyl group, in which a single carbon spacer unit is attached to an aryl group, where the carbon spacer and the aryl group can be optionally substituted as described herein.

The terms "arylalkenyl" mean an alkenyl substituted with one or more aryl groups, wherein the alkenyl and aryl groups are as herein described. One particular example is an arylethenyl group.

The term "substituted" or "optionally substituted" is used to indicate that a group may have a substituent at each substitutable atom of the group (including more than one substituent on a single atom), provided that the designated atom's normal valency is not exceeded and the identity of each substituent is independent of the others. Up to three H atoms in each residue are replaced with alkyl, halogen, haloalkyl, hydroxy, lower alkoxy, carboxy, carboalkoxy (also referred to as alkoxycarbonyl), carboxamido (also referred to as alkylaminocarbonyl), cyano, carbonyl, nitro, amino, alkylamino, dialkylamino, mercapto, alkylthio, sulfoxide, sulfone, acylamino, amidino, phenyl, benzyl, heteroaryl, phenoxy, benzyloxy, or heteroaryloxy. "Unsubstituted" atoms bear all of the hydrogen atoms dictated by their valency. When a substituent is keto (i.e., =O), then two hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious therapeutic agent.

The term "fatty acid" generally refers to a carboxylic acid which bears a hydrocarbon radical. The hydrocarbon radical has been described above, and can have from about 4 to 50 carbon atoms in length. Typical fatty acids have 4 to 30 carbon atoms, 4 to 28 carbon atoms, 8 to 26 carbon atoms, 8 to 24 carbon atoms, 8 to 22 carbon atoms, 12 to 22 carbon atoms, 12 to 18 carbon atoms, 14 to 22 carbon atoms, or 15 to 18 carbon atoms. They may be of a natural or synthetic origin. Fatty acids can be saturated, unsaturated, or polyunsaturated. When they are unsaturated, they may contain one or more, for example two, three or more, double bonds.

The above terms "hydrocarbon radical", "alkyl", "aryl", and "fatty acid" may be optionally substituted, substituted or unsubstituted.

Compounds described herein may contain one or more asymmetric centers and may thus give rise to enantiomers, diastereomers, and other stereoisomeric forms. Each chiral center may be defined, in terms of absolute stereochemistry, as (R)- or (S)-. This technology is meant to include all such possible isomers, as well as mixtures thereof, including racemic and optically pure forms. Optically active (R)- and (S)-, (−)- and (+)-, or (D)- and (L)-isomers may be prepared using chiral synthons or chiral reagents, or resolved using conventional techniques. Likewise, all tautomeric forms are also intended to be included.

One aspect of the invention relates to a fatty acid amide compound having the Formula (I):

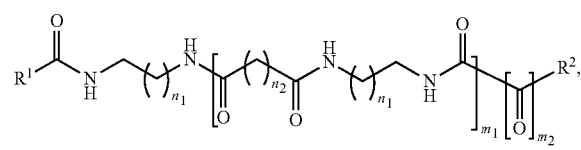

wherein:

$R^1$ a substituted or unsubstituted $C_3$ to $C_{50}$ alkyl or substituted or unsubstituted aryl;

$R^2$ is H, substituted or unsubstituted $C_3$ to $C_{50}$ alkyl, substituted or unsubstituted arylalkyl, substituted or unsubstituted arylalkenyl, or substituted or unsubstituted aryl;

$n_1$ is an integer from 0 to 10;

$n_2$ is an integer from 1 to 20;

$m_1$ is 0 or 1; and $m_2$ is 0 or 1, and wherein $m_1+m_2$ cannot be 2.

In one embodiment the fatty acid amide compound of Formula (I) has Formula (Ia):

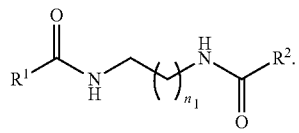

In another embodiment the fatty acid amide compound of Formula (I) has Formula (Ib):

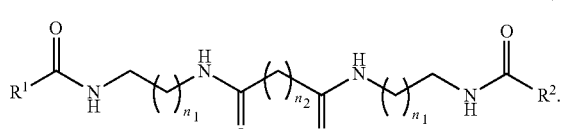

In another embodiment the fatty acid amide compound of Formula (I) has Formula (Ic):

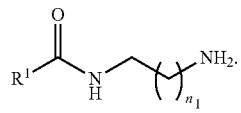

Another embodiment relates to the fatty acid amide compound of Formula (I) where $m_1$ is 0; $m_2$ is 0; and $R^2$ is H.

Yet another embodiment relates to the fatty acid amide compound of Formula (I) where $m_1$ is 0; $m_2$ is 1; and $R^2$ is a substituted or unsubstituted $C_3$ to $C_{50}$ alkyl, substituted or unsubstituted arylalkyl, or substituted or unsubstituted arylalkenyl.

Another embodiment relates to the fatty acid amide compound of Formula (I) where $m_1$ is 1; $m_2$ is 0; and $R^2$ is a substituted or unsubstituted $C_3$ to $C_{50}$ alkyl.

Yet another embodiment relates to the fatty acid amide compound of Formula (I) where $n_2$ is an integer from 6 to 12.

Another aspect of the invention relates to a wax composition comprising a plurality of fatty acid amide compounds having the Formula (I):

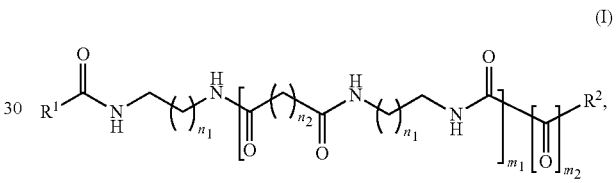

wherein:

$R^1$ a substituted or unsubstituted $C_3$ to $C_{50}$ alkyl or substituted or unsubstituted aryl;

$R^2$ is H, substituted or unsubstituted $C_3$ to $C_{50}$ alkyl, substituted or unsubstituted arylalkyl, substituted or unsubstituted arylalkenyl, or substituted or unsubstituted aryl;

$n_1$ is an integer from 0 to 10;

$n_2$ is an integer from 1 to 20;

$m_1$ is 0 or 1; and $m_2$ is 0 or 1, and wherein $m_1+m_2$ cannot be 2.

One embodiment relates to the wax composition comprising compounds of Formula (I) where $m_1$ is 0; $m_2$ is 0; and $R^2$ is H.

Another embodiment relates to the wax composition comprising compounds of Formula (I) where $m_1$ is 0; $m_2$ is 1; and $R^2$ is a substituted or unsubstituted $C_3$ to $C_{50}$ alkyl, substituted or unsubstituted arylalkyl, or substituted or unsubstituted arylalkenyl.

Another embodiment relates to the wax composition comprising compounds of Formula (I) where $m_1$ is 1; $m_2$ is 0; and $R^2$ is a substituted or unsubstituted $C_3$ to $C_{50}$ alkyl.

Yet another embodiment relates to the wax composition comprising compounds of Formula (I) where $n_2$ is an integer from 6 to 12.

The wax composition can have a melting point ranging from 40° C. to 250° C., for instance, from 50° C. to 200° C., or from 80° C. to 200° C.

The wax composition has a penetration hardness of 5.0 mm or below (i.e., a penetration distance), for instance, 4.0 mm or below, 3.0 mm or below, 2.0 mm or below, 1.0 mm or below, 0.5 mm or below, or 0.1 mm or below. The penetration hardness is measured by a standard needle penetration test according to the ASTM D1321 standard, with a 100 g cone and the penetration being conducted for 5 seconds at 23° C.

Another aspect of the invention relates to a wax composition comprising:

a) one or more fatty acid amide compounds having the Formula (II):

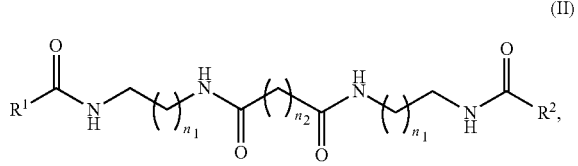

(II)

and b) one or more fatty acid amide compounds having the Formula (III):

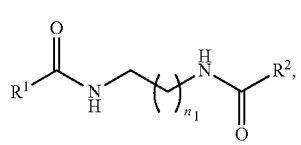

(III)

wherein:

$R^1$ is each independently a substituted or unsubstituted $C_3$ to $C_{50}$ alkyl or substituted or unsubstituted aryl;

$R^2$ is each independently substituted or unsubstituted $C_3$ to $C_{50}$ alkyl, substituted or unsubstituted arylalkyl, substituted or unsubstituted arylalkenyl, or substituted or unsubstituted aryl;

$n_1$ is an integer from 0 to 10; and $n_2$ is an integer from 1 to 20;

wherein component a) and component b) are blended together.

One embodiment relates to the wax composition further comprising: c) one or more fatty acid monoamide compounds having the Formula (IV):

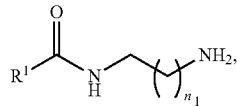

(IV)

wherein $R^1$ is a substituted or unsubstituted $C_3$ to $C_{50}$ alkyl or aryl; and $n_1$ is an integer from 0 to 10

Another embodiment relates to the wax composition comprising compounds of Formula (I) where $R^1$ is each independently a substituted or unsubstituted $C_{12}$ to $C_{50}$ alkyl or substituted or unsubstituted aryl; $R^2$ is each independently substituted or unsubstituted $C_{12}$ to $C_{50}$ alkyl, substituted or unsubstituted arylalkyl, substituted or unsubstituted arylalkenyl, or substituted or unsubstituted aryl; and $n_2$ is an integer from 6 to 20.

Another embodiment relates to the wax composition comprising compounds of Formula (I) where $R^1$ is each independently an unsubstituted $C_3$ to $C_{28}$ alkyl, and $R^2$ is each independently substituted or unsubstituted $C_3$ to $C_{28}$ alkyl or substituted or unsubstituted arylalkenyl.

Yet another embodiment relates to the wax composition comprising compounds of Formula (I) where $R^1$ is each independently an unsubstituted $C_{12}$ to $C_{28}$ alkyl, and $R^2$ is each independently substituted or unsubstituted $C_{12}$ to $C_{28}$ alkyl or substituted or unsubstituted arylalkenyl.

A further embodiment relates to the wax composition comprising compounds of Formula (I) where $R^1$ is a substituted or unsubstituted $C_{12}$ to $C_{50}$ alkyl or aryl.

In the wax composition containing a blend of component a) and component b), the component a) can range from 10 wt % to 99 wt % of the wax composition, for instance, from 20 wt % to 90 wt %, from 60 wt % to 90 wt %, or from 90 wt % to 95 wt % of the wax composition. The component b) can range from 1 wt % to 90 wt % of the wax composition, for instance, from 10 wt % to 80 wt %, from 10 wt % to 50 wt %, or from 10 wt % to 40 wt % of the wax composition. When the concentration of the component b) is too high, the wax composition may become too soft or become a liquid at ambient temperature, which may be undesirable for its application as wax.

One embodiment relates to the wax composition where the component a) ranges from 20 wt % to 90 wt % of the wax composition, and the component b) ranges from 10 wt % to 80 wt % of the wax composition.

Another embodiment relates to the wax composition where the component a) ranges from 60 wt % to 90 wt % of the wax composition, and the component b) ranges from 10 wt % to 40 wt % of the wax composition.

Another embodiment relates to a coated material comprising the wax composition as described in any of the preceding paragraphs and a substrate, where the wax composition is coated on the substrate.

Another aspect of the invention relates to a process for preparing a compound of Formula (I):

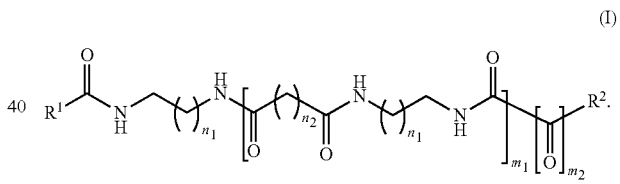

(I)

This process comprises:

providing one or more monoamide compounds having the Formula (IV):

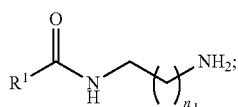

(IV)

providing one or more acids having the Formula (V)

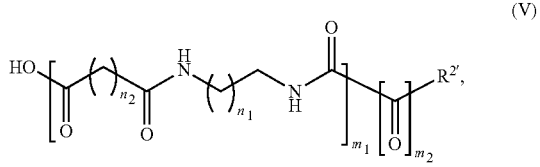

(V)

wherein
R$^1$ is a substituted or unsubstituted C$_3$ to C$_{50}$ alkyl;
R$^2$ is OH, substituted or unsubstituted C$_3$ to C$_{50}$ alkyl, substituted or unsubstituted arylalkyl, substituted or unsubstituted arylalkenyl, or substituted or unsubstituted aryl;
n$_1$ is an integer from 0 to 10;
n$_2$ is an integer from 1 to 20;
m$_1$ is 0 or 1; and
m$_2$ is 0 or 1,
wherein m$_1$+m$_2$ cannot be 2; and
reacting the one or more monoamide compounds having the Formula (IV) with the one or more acids having Formula (V) under conditions effective to make the compound of Formula (I).

The reaction of monoamide compound(s) with acid(s) can be carried out over a wide range of temperatures. Typically, the reaction is carried out at a temperature no higher than 200° C., for instance, at a temperature ranging from 60 to 160° C., from 90 to 150° C., from 60 to 120° C., from 70 to 100° C., or from 80 to 95° C. The duration of this reaction can be over a broad range of times. Typically, an almost complete conversion of monoamide compound to the corresponding compound of Formula (I) can be achieved in 12 hours or less, in 6 hours or less, or in 3 hours or less.

One embodiment relates to the process for preparing a compound of Formula (I), where said providing one or more monoamide compounds having the Formula (VI) comprises:
providing one or more saturated free fatty acids having the Formula (VI)

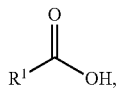

(VI)

wherein R$^1$ is a substituted or unsubstituted C$_3$ to C$_{50}$ alkyl;
providing a diamine compound having the Formula (VII)

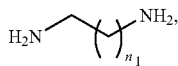

(VII)

wherein n$_1$ is an integer from 0 to 10; and
reacting the diamine compound having the Formula (VII) with the one or more saturated free fatty acids having the Formula (VI) to form the one or more monoamide compounds of Formula (IV).

The fatty acids used in this invention are saturated free fatty acids. The term "fatty acid" has been described herein. Typically, the saturated free fatty acid used herein has the formula of

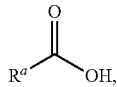

wherein R$^a$ is a substituted or unsubstituted C$_4$ to C$_{50}$ alkyl. For instance, R$^a$ is a substituted or unsubstituted C$_4$ to C$_{28}$ alkyl, a substituted or unsubstituted C$_8$ to C$_{26}$ alkyl, a substituted or unsubstituted C$_8$ to C$_{22}$ alkyl, a substituted or unsubstituted C$_{14}$ to C$_{22}$ alkyl, or a substituted or unsubstituted C$_{15}$ to C$_{18}$ alkyl. Typically, R$^a$ is an unsubstituted alkyl.

The saturated free fatty acids may be derived from a natural or synthetic fatty acid. The saturated free fatty acids herein can vary depending on the source of fatty acids used. Exemplary fatty acid sources include butyric acid, caproic acid, caprylic acid, capric acid, decenoic acid, lauric acid, cis-9-dodecenoic acid, myristic acid, myristoleic acid, cis-9-tetradecenoic acid, pentadecanoic acid, palmitic acid, palmitoleic acid, cis-9-hexadecenoic acid, heptadecanoic acid, heptadecenoic acid, stearic acid, oleic acid, linoleic acid, linolenic acid, α-linolenic acid ricinoleic acid, dihydroxystearic acid, nonadecanoic acid, arachidic acid, cis-9 acid, cis-11-eicosenoic acid, eicosadienoic acid, eicosatrienoic acid, arachidonic acid, eicosapentaenoic acid, behenic acid, erucic acid, docosadienoic acid, 4,8,12,15,19-docosapentaenoic acid, docosahexaenoic acid, lignoceric acid, tetracosenoic acid, and mixtures thereof. Any of the above fatty acids can be fully hydrogenated to prepare the saturated free fatty acids.

Additionally, suitable saturated free fatty acids or mixture thereof can also be obtained from fully hydrogenated fats or vegetable oil, by methods known to one skilled in the art. For instance, saturated free fatty acids used in the present invention can be produced from fully hydrogenated vegetable oils via a saponification process followed by an acidification process as described in Ferdous et al., "Preparation and Optimization of Biodiesel Production from Mixed Feed Stock Oil," *Chemical Engineering and Science* 1 (4): 62-66 (2011), which is hereby incorporated by reference in its entirety, and optionally with minor modifications. The major components in most vegetable oils are triacylglycerols (TAGs). The physical properties of TAGs depend on the length of the fatty acyl chains, the amount and type of unsaturation in the fatty acid chains, and the distribution of fatty acyl groups among the sn-positions of the TAGs (U.S. Pat. No. 6,824,572 to Murphy, which is hereby incorporated by reference in its entirety). Exemplary fully hydrogenated fats or vegetable oils are fully hydrogenated soybean oil, fully hydrogenated cottonseed oil, fully hydrogenated sunflower oil, fully hydrogenated canola oil, fully hydrogenated corn oil, fully hydrogenated palm oil, fully hydrogenated olive oil, fully hydrogenated peanut oil, fully hydrogenated safflower oil, fully hydrogenated coconut oil, fully hydrogenated rapeseed oil, fully hydrogenated castor oil, fully hydrogenated mustard seed oil, fully hydrogenated tallow oil, fully hydrogenated bone oil, fully hydrogenated fish oil, fully hydrogenated tall oil, or mixtures thereof. These hydrogenated fats or vegetable oils are readily commercially available. Alternatively, hydrogenated fats or vegetable oils can be made by processes known in the art. Typically, the fatty acids used herein are a mixture of saturated free fatty acids prepared from fully hydrogenated soybean oil.

The diamines used herein are aliphatic diamines having a formula

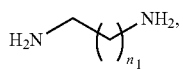

wherein n$_1$ is an integer from 0 to 30, from 0 to 20, from 0 to 15, from 0 to 10, from 0 to 5. Exemplary diamines include ethylene diamine, 1,3-diaminopropane, 1,4-diaminobutane, and 1,6-hexamethylene diamine. The diamines may be commercially available, or prepared by methods known to one skilled in the art.

The reaction of free fatty acid with diamine can be carried out over a wide range of temperatures. Typically, the reaction is carried out at a temperature no higher than 200° C., for instance, at a temperature ranging from 60 to 160° C., from 90 to 150° C., from 60 to 120° C., from 70 to 100° C., or from 80 to 95° C. The duration of this reaction can be over a broad range of times. Typically, an almost complete conversion of saturated free fatty acid to the corresponding monoamide compound can be achieved in 12 hours or less, in 6 hours or less, or in 3 hours or less.

The saturated free fatty acid used for preparing monoamide compounds is typically but not limited to an equal molar amount or an excess molar amount than the diamine compound. Thus, the diamine compound, or mixture thereof to the saturated free fatty acid molar ratio is equal to or less than 1. The molar ratio of the diamine compound, or mixture thereof to the saturated free fatty acid depends on the desirable amount of fatty acid monoamide in the fatty acid amide product. When the molar ratio of the diamine compound, or mixture thereof to the saturated free fatty acid is equals to or less than 1:2, the product contains mainly fatty acid diamides. When the molar ratio of the diamine compound, or mixture thereof to the saturated free fatty acid is equal to or less than 1 but greater than 1:2, the product contains a mixture of fatty acid monoamide/diamider. The product can contain mainly fatty acid monoamides when the molar ratio of the diamine compound, or mixture thereof to the saturated free fatty acid is about 1 or greater. Typically, the molar ratio of the diamine compound, or mixture thereof to the one or more saturated free fatty acid typically ranges from 1.5:1 to 1:3, for instance, from 1:1 to 1:2, from 1:1 to 1:1.5, from 1:1 to 1:1.1, or from 1.5:1 to 1:1.

When the starting material for the reaction contains one or more different saturated free fatty acids, the resulting wax composition can contain a mixture of different fatty acid ester compounds, with the amide groups resulting from different fatty acids. This is the case when the saturated free fatty acid is obtained from fully hydrogenated fats or vegetable oil, because these fats or vegetable oils typically contain a mixture of triglycerides having a variety of fatty acid residues. For example, a typical fatty acid composition in soybean oil is as shown in Table 1 below.

TABLE 1

A Typical Fatty Acid Composition in Soybean Oil.

| Fatty acid | Weight Percent[1] |
| --- | --- |
| Palmitic acid | 10.5 |
| Stearic acid | 4.5 |
| Oleic acid | 23.0 |
| Linoleic acid | 53.0 |
| Linolenic acid | 7.5 |
| Other | 1.5 |

[1]Weight percent of total fatty acid mixture derived from hydrolysis of soybean oil.

The wax compositions of the present invention can be employed as pure substances or can be mixed with other wax components known to one skilled in the art, such as paraffin or beeswax, polyethylene waxes, polypropylene waxes, amide waxes, Fischer-Tropsch waxes, and the like.

In one embodiment, the wax composition further comprises one or more natural waxes.

Natural waxes that can be used in accordance with the present invention include candelilla, carnauba, beeswax, bayberry-myrtle, castor bean wax, esparto grass wax, Japan wax, ouricury, retamo-ceri mimbi, shellac wax, spermaceti, sugar cane wax, wool wax-lanolin, jojoba, montan, peat wax, ouricury wax, soy wax, esparto wax, rice wax, maize wax, or bayberry wax.

The wax compositions can be dissolved in solvents at an elevated temperature and be precipitated via cooling. Pastes thus prepared can be used in print applications for control of viscosity and of slip behavior.

The wax compositions of the present invention can be used to prepare a coated material. The coated material comprises the wax composition described supra and a substrate. The liquid or melted wax composition is used to encase the substrate.

Any method for packaging a wax material which results in wax-coated material having a finite size and shape using a film to surround the substrate is in general suitable. For example, three common techniques for adding a wax to a substrate (e.g., a corrugated board), i.e., curtain coating, wax cascading, and wax impregnation, can be used herein. In the curtain coating method, the wax composition with a melting temperature of about 75-80° C. is blended with other packaging compositions to create a blend that reduces the wax fracturing on the score lines of the corrugated board. The wax cascading method uses the wax composition with a melting temperature of about 60° C., with the corrugated sheets placed vertically as they pass through a waterfall of a molten wax. The wax impregnation method applies the wax composition to a corrugated board on a corrugator.

The coated material may also be prepared in a manner analogous to the methods for packaged hot melt adhesives as described in WO 02/061009, WO 04/037671, and U.S. Pat. Nos. 6,230,890, 5,806,285, 5,401,455, 5,715,654, and 4,039,485, which are hereby incorporated by reference in their entirety.

A wide variety of substrates (such as packaging substrates), well known in the art of package making, can be used in preparing the coated materials. For instance, a cardboard, or a thermoplastic polymer composition.

Suitable thermoplastic polymer compositions include, but are not limited to, polypropylene, polyethylene and copolymers thereof, terpolymers of ethylene and ethylene/vinyl acetate, ethylene acrylate, ethylene methacrylate, ethylene methyl acrylate, ethylene methyl methacrylate, copolymers of ethylene and 1,6-mono- or di-unsaturated monomers, polyamides, polybutadiene rubber, polyesters such as polyethylene terephthatate, polybutylene terephthalate, polycarbonates, atactic poly-alpha-olefins, including atactic polypropylene, thermoplastic polyacrylamides, polyacrylonitrile, copolymers of acrylonitrile and other monomers such as butadiene, styrene, polymethyl pentene, polyphenylene sulfide, aromatic polyurethanes; styrene-acrylonitrile, acrylonitrile-butadiene-styrene, styrene-butadiene rubbers, acrylonitrile-butadiene-styrene elastomers. Suitable thermoplastic polymer compositions also include block copolymers comprising a polyvinyl aromatic block and a rubbery midblock which can be partly hydrogenated. The thermoplastic polymer composition may form a continuous film, a woven material, or non-woven material.

The wax composition of the invention can also be used in agricultural products, e.g., in fertilizer production and formulation. The wax composition of the invention may be used for time-released coatings, moisture- and water-barrier coatings, dust and fines control coatings, and inert carriers for ingredients. For instance, the wax composition of the invention may be formulated in a manner that provides a hard, non-cracking, water resistant fertilizer coating that breaks down over time, allowing for the controlled release of plant nutrients.

Accordingly, some embodiments of the present invention provide a biodegradable coating comprising the wax composition described supra and an emulsifier.

Any method for applying the biodegradable coating to the agricultural products is in general suitable. For instance, the biodegradable coating can be applied to the surface of a plant by rubbing the biodegradable coating onto the surface of the plant (e.g., by using of rubber gloves), by dipping or immersing the plant in the biodegradable coating, by spraying the biodegradable coating onto the plant, pouring the biodegradable coating onto the plant (e.g., when the plant is moving on a conveyor belt).

A wide variety of emulsifiers, well known in the art of food or plant coatings, can be used in preparing the packaging materials. In certain embodiments, the emulsifier is an edible emulsifier selected from non-ionic emulsifier, anionic emulsifier, and mixtures thereof. In some embodiments, the emulsifier enables the wax composition to be in a liquid form at room temperature. The emulsifier may facilitate the solubility of the wax composition in the coating. The emulsifier may serve as a pH modifier of the coating. Nonlimiting examples of suitable emulsifiers include morpholine, ammonia, lecithin, ethylene glycol monostearate, ammonium lauryl sulfate, sodium steroyl-2-lactylate, potassium oleate, propylene glycol monostearate, sodium alkyl sulfate, and polyglycol.

EXAMPLES

Example 1

Materials for Examples 2-7

Fully hydrogenated soybean oil (FHSO) was provided by Stratas Food (Memphis, Tenn.). Hydrogenated castor oil (HCO) was provided by Acme-Hardesty CO (Blue bell, Pa.). Carnauba wax was provided by Michelman Inc. (Cincinnati, Ohio). Ethanolamine (ETA), ethylenediamine (ETD), cinnamic acid, dodecanedioic acid, and other chemicals were purchased from Sigma-Aldrich (St. Louis, Mo.).

Example 2

Preparation of Saturated Free Fatty Acid (SFFA) from FHSO

SFFA was produced from FHSO by a modified saponification then acidification process (Ferdous et al. "Preparation and Optimization of Biodiesel Production from Mixed Feed Stock Oil," *Chemical Engineering and Science* 1 (4): 62-66 (2011), which is hereby incorporated by reference in its entirety). FHSO was mixed with aqueous sodium hydroxide solution (4 M) and the molar ratio of oil to sodium hydroxide was 1:3. The mixture was heated at 100° C. for 1 hour under reflux with vigorous mixing to form a soap solution. Hydrochloric acid was then added to acidify the soap solution, and molar ratio of soap to HCl was 1:1.5. The mixture was heated at 100° C. for 1 hour and then cooled to room temperature. SFFA was collected upon solidification and vacuum oven dried. This SFFA contained 11 wt % C16 and 89 wt % C18 fatty acid. For the simplicity of expression and discussion, carbon chain length of 18 was used for this material.

Example 3

Syntheses of Monoamide, Diamide, and Diester with Functional Groups

The SFFA prepared was used to react with ETD to form fatty acid monoamide and diamide. Molten SFFA was slowly added to ETD at an equivalent molar ratio of (COOH to NH$_2$) 1:2, 1:3, and 1:4 in a round bottom flask connected with a reflux condenser, and the system was then heated at 90, 110, 130, and 150° C. for 3 hours to determine the effect of temperature on reaction completeness. After the reaction, the flask was disconnected and heated for another 30 minutes to evaporate any ETD residue. The mixture of mono and diamide were characterized by $^1$H-NMR and the proportion of mono and diamide was determined.

To attach a benzene ring structure, cinnamic acid was used to react with the monoamide in the mixture from the steps above. To evaluate the effect of diacid reacting with the free —NH$_2$ group and increasing chain length on texture properties, adipic acid (C6) and dodecanedioic acid (C12) were selected to link two units of monoamide. The reactants were mixed in a round bottom flask (molar ratio of —NH$_2$ group in monoamide to acid group equal to 1:1) and then heated at 150° C. for 2 hours. The overall reaction design is shown in Scheme 1 below.

Scheme 1. Chemical Reaction Route for Synthesis of Carnauba Wax Substitute

Reaction 1: Formation of monoamide with free amine group and short chain diamide

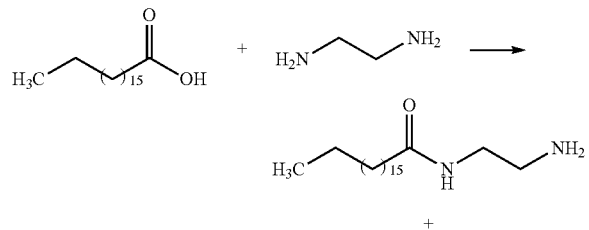

Short chain diamide C38

Reaction 2: Linkage of two monoamide with free amine by C6 or C12 diacid

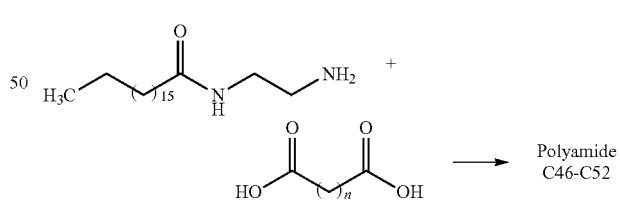

Polyamide C46-C52

Reaction 3: Reacting of free amine group in the monoamide with cinnamic acid

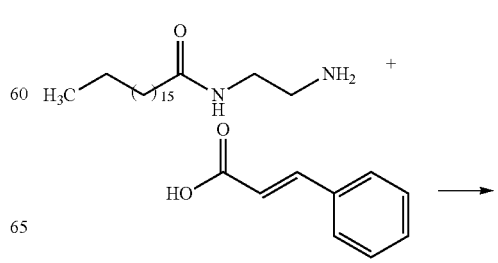

-continued

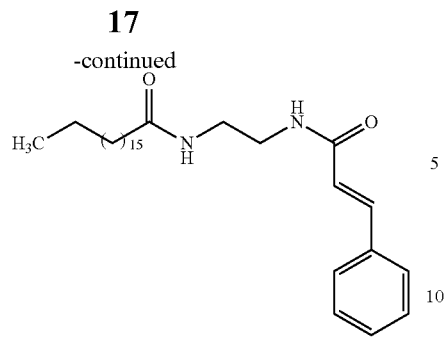

The starting material for Reactions (2) and (3) was the mixture generated in Reaction (1). The materials from all reactions are mixtures, which can be described as follows. Mixture $\hat{1}$ is a mixture of monoamide with a free amine group and short chain diamide from reaction 1. Mixture $\hat{2}$ is a mixture of polyamide (i.e., two monoamides linked by a diacid) and short chain diamide from reaction 1. Mixture $\hat{3}$ is a mixture of diamide with ring structure (R-diamide) and short chain diamide from reaction 1.

Material $\hat{2}$ which has the optimal content of polyamide was selected for mixing with the corresponding material $\hat{3}$ to form material $\hat{4}$. To make this mixture, 5, 10, 15, 20, 30, and 50 wt % of the selected material $\hat{3}$ was substituted for mixture $\hat{2}$. The two materials were molten at 5° C. above their melting temperatures and mixed by continuous stirring for 5 minutes. The mixture was collected on solidification and used for textural analyses.

To synthesize long chain diester that has same chain length as the polyamide, SFFA was mixed with 1,16-hexadecanediol at a molar ratio of 2:1 in a round bottom flask. The mixture was then heated for 12 hours at 95° C. with 5 wt % of amberlyst-15 as catalyst. After reaction, hot filtration was used to remove the catalyst, and the liquid sample was cooled, collected, and saved for textural analyses. This material was used to compare the properties displayed by diester vs. polyamide, as well as to be blended with long-chain fatty alcohols.

The unsaponifiable matters containing long-chain fatty alcohols was obtained from carnauba wax following the procedure reported by Yildiz (Yildiz et al., "Unsaponifiable Matter in Carnuba (Cera carnuba) Wax, a Modification of the USP/NF and FCC Methods," *Am. J. Anal. Chem.* 7:611-616 (2016), which is hereby incorporated by reference in its entirety) with minor modifications. Carnauba wax was saponified by refluxing for 1 hour with continuous stirring in 1.25 M sodium hydroxide ethanol solution. After saponification, heptane was added to the cooled solution. The system was refluxed again until a homogeneous clear solution was observed. Two layers were formed after cooling and the top heptane layer, which contained the fatty alcohols, was collected. This heptane layer was washed 3 times using hot distilled water, and then the solvent was removed by rotary evaporator at 95° C. The residue was collected and dried in a vacuum oven at 105° C.

Example 4

Synthesis of Carnauba Substitute Using FHSO Directly

To explore the possibility of developing a feasible and more economical synthesis procedure, FHSO instead of SFFA was used to repeat the reaction. The optimal reactant ratio and reaction conditions determined in the previous steps were used. Mixture of FHSO and ETD was heated at the optimal temperature for 3 hours and the monoamides formed in the reaction were reacted with diacid and cinnamic acid. The proportion of diacid and cinnamic acid used was calculated based on the optimal blending ratio determined in the above section.

Example 5

Characterization and Textural Analysis of the Mixtures

To evaluate the effect of SFFA to ETD reactant ratio, reaction temperature and time on distribution of monoamide with free amine on the terminal end and diamide in material $\hat{1}$, $^1$H NMR spectra of the mixtures were obtained using a Bruker A VIII-600 (Rheinstetten, Germany), and the proportion of mono and diamide was determined by integrating the respective areas. The samples were prepared in CDCl$_3$. The ratio of monoamide to total amide was determined and expressed as percentage of monoamide in final product. Monoamide with active amine group: δ=2.3 (2H,

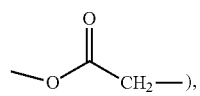

δ=3.3 (2H, —NH$_2$),

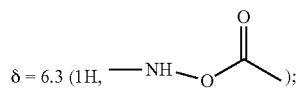

Diamide:

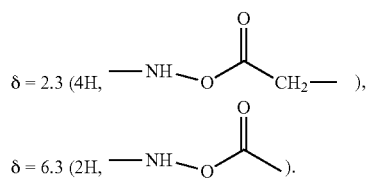

Hardness of the materials was measured using a universal penetrometer (BCL-466, Certified Material Testing Products, Palm Bay, Fla.) following ASTM method D1321. Penetration was measured by applying a standard needle to the sample (thickness of about 20 mm) for 5 s under a load of 100 g. The inverse of the distance that the standard needle penetrated into the wax surface was defined as hardness, and a higher value represents higher hardness.

Surface hydrophobicity of the optimal carnauba wax substitute was evaluated by using a contact angle goniometer (Rame-Hart, Model 250; Succasunna, N.J.). Wax samples with a thickness of about 2 mm were prepared using a disc mold. A water droplet was applied on the bottom surface of the sample, and water contact angle was taken at 3 min.

Topography of the waxes was evaluated using a Hyperspectral Microscope (S-neox, Sensofar Metrology, Scottsdale, Ariz.). The wax samples were molten at 5° C. above their melting temperatures, and then one drop of the molten wax was placed on a microscopy slide and allowed to stabilize for 1 hour. Three-dimensional surface images of the waxes were then obtained. The image RMS (Rq) which is the root mean square average of height deviations taken from the mean data plane was calculated using the Sensofar Metrology software, and Rq in micrometer (mm) was used to represent surface roughness of the wax samples. The surface friction and adhesion of the wax samples were evaluated using an Atomic Force Microscopy (AFM Dimension Icon, Brucker, Billerica, Mass.) following the methods reported by Attard (Attard et al., "Measurement of Friction Coefficients with the Atomic Force Microscope," *J. Phys. Conf. Ser.* 61:51-55 (2007), which is hereby incorporated by reference in its entirety) and Duong (Duong et al., "Surface Roughness and Frictional Coefficient of Hip Implant Using Atomic Force Microscopy," 55th Annual Meeting of the Orthopaedic Research Society, Poster No. 2324 (2009), which is hereby incorporated by reference in its entirety), with modifications. An AFM probe (SNL-10, Bruker, Billerica, Mass.) with a silicon-tip on a nitride lever and a normal spring constant of KN=0.06 nN/nm was used. A static discharge device was used to reduce the electrostatic forces on samples prior to AFM data collection. Vertical force was normalized and kept constant across all samples and a flat region was selected for a 100 nm scan to minimize the contribution of topography to friction. The probe was programed to go through trace-retrace and extend-retract cycles, and the corresponding force curves were recorded. The curves were analyzed using Nanoscope Analysis (Bruker, Billerica, Mass.). The average difference in lateral force (voltage) signals between the trace and retrace curves was used as the indicator of surface friction (Duong et al., Surface roughness and frictional coefficient of hip implant using atomic force microscopy, 55th Annual Meeting of the Orthopaedic Research Society Poster (2009), which is hereby incorporated by reference in its entirety), and attraction and rupture forces were calculated using the following equation to evaluate adhesion.

Force (nN)=$K_n$ (nN/mm)×displacement (nm)

Surface gloss of the selected waxes was measured using a WG60 Precision Glossmeter. Waxes were molten and recrystallized into 30 mm×10 mm strips, and gloss was measured at a 60° angle from normal to the sample surface.

Surface coefficient of friction of the waxes was evaluated using Atomic Force Microscopy (Dimension 3000, Digital Instruments/Veeco Metrology, Plainview, N.Y.) following the method reported by Breajsoear et al. "Friction Coefficient Mapping Using the Atomic Force Microscope," *Surf Interface Anal.* 36:1330-1334 (2004), which is hereby incorporated by reference in its entirety.

Example 6

Thermal Analysis of Different Wax Mixtures

The melting and crystallization properties of the waxes were analyzed using a differential scanning calorimeter (DSC-7, Perkin-Elmer, Norwalk, Conn.) equipped with an Intracooling II system. Solid wax (about 10 mg) was weighed into a steel pan (Perkin-Elmer) and the pan was sealed. A blank steel pan was used as reference. The temperature program started with a 10-min hold at 20° C., followed by 20° C./min heating to 200° C. and a 5-min hold at 200° C. The melting point peak was captured during the heating step and calculated using Pyris software (Perkin-Elmer, Norwalk, Conn. USA). The peak was then used to compare with that of the control. Three replicates from each wax sample were measured.

Example 7

Statistical Analysis

Three batches of wax were synthesized for each treatment. Each batch of wax was used to provide three samples for the textural, thermal, and compositional analysis. Treatment effects were examined at the 5% significance level using Statistical Analysis System (SAS) 9.1 (SAS Institute, Cary, N.C.). The means and standard deviations were determined and presented.

Example 8

Results and Discussion of Examples 1-7

Figure 1B:
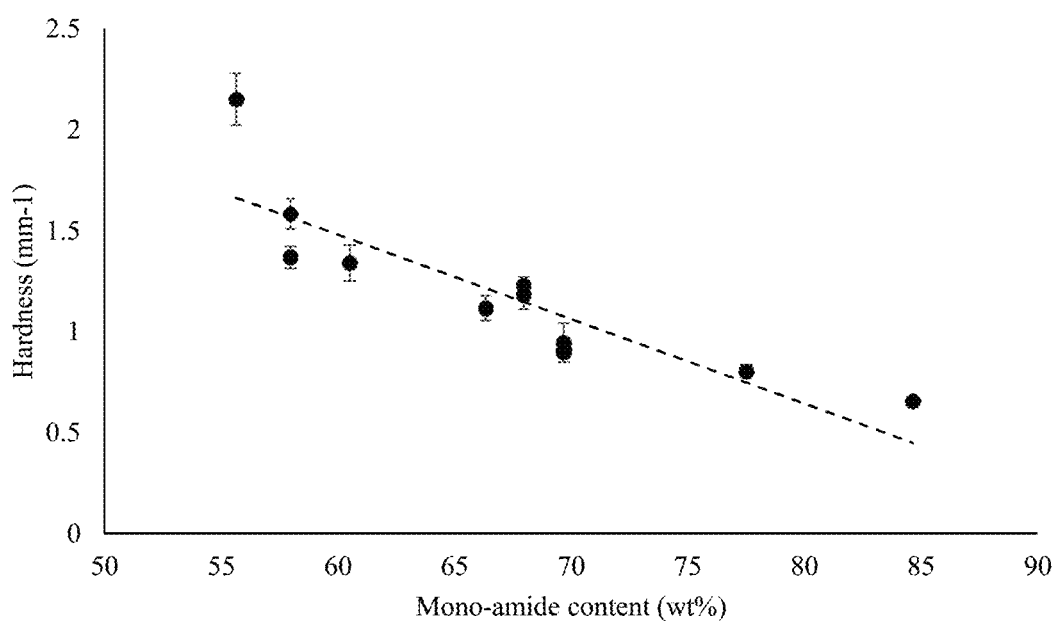

Effect of Reactant Ratio and Reaction Temperature on Monoamide Formation and Subsequently on Hardness $^1$H NMR was used to characterize the composition of the mixture $\hat{1}$, and proportion of short chain diamide and monoamide with a free amine group was determined. FIG. 1A shows the content of monoamide obtained at different temperatures with different mixing ratio of SFFA to ethylenediamine. No clear trend of effect of reactant ratio and temperature on monoamide formation was observed. However, a clear trend of effect of monoamide content on hardness of the material was observed. FIG. 1B shows that higher content of monoamide led to lower hardness of the material. The lower hardness is probably due to the shorter chain length of the monoamide (20 C). Higher content of monoamide led to a lower average chain length of the material, and thus a reduced hardness. Fatty acyl chain length significantly affected chemical and thermal stability of oil based materials, and longer chain led to higher stability and hardness (Abes et al, "Crystallization and Phase Behavior of Fatty Acid Esters of 1,3-Propanediol I: Pure System," *Chem. Phys. Lipids.* 149:14-27 (2007); Raghunanan L et al., "Influence of Structure on Chemical and Thermal Stability of Aliphatic Diesters," *J Phys. Chem. B.* 117:14753-14762 (2013), which are hereby incorporated by reference in their entirety).

A reactant molar ratio (COOH to $NH_2$) of 1:1 and heating temperature of 130° C. covered were selected as optimal conditions for reaction 1. Such condition produced mixture $\hat{1}$ containing 78% of monoamide with reactive amine group and 22% of C38 short chain diamide, which then subsequently led to a mixture $\hat{2}$ consisting of about 90 wt % C52 polyamide and 10 wt % of C38 short chain diamide with reaction 2; and a mixture $\hat{3}$ consisting of 83 wt % of C23 diamide with cinnamic ring and 17 wt % of C38 short chain diamide with reaction 3. Mixtures $\hat{2}$ and $\hat{3}$ were then saved for subsequent mixing to test the effect of cinnamic rings on surface properties and hardness of the material.

Figure 2:
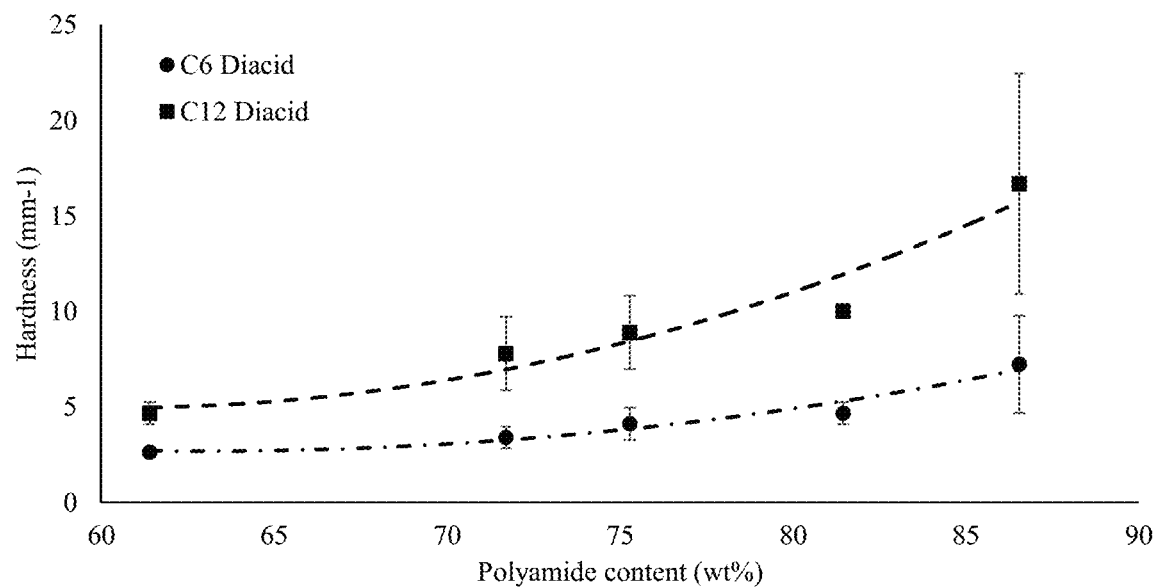
FIG. 2 is a graph showing effect of carbon chain length and long chain diamide content on hardness.
Figure 3A:
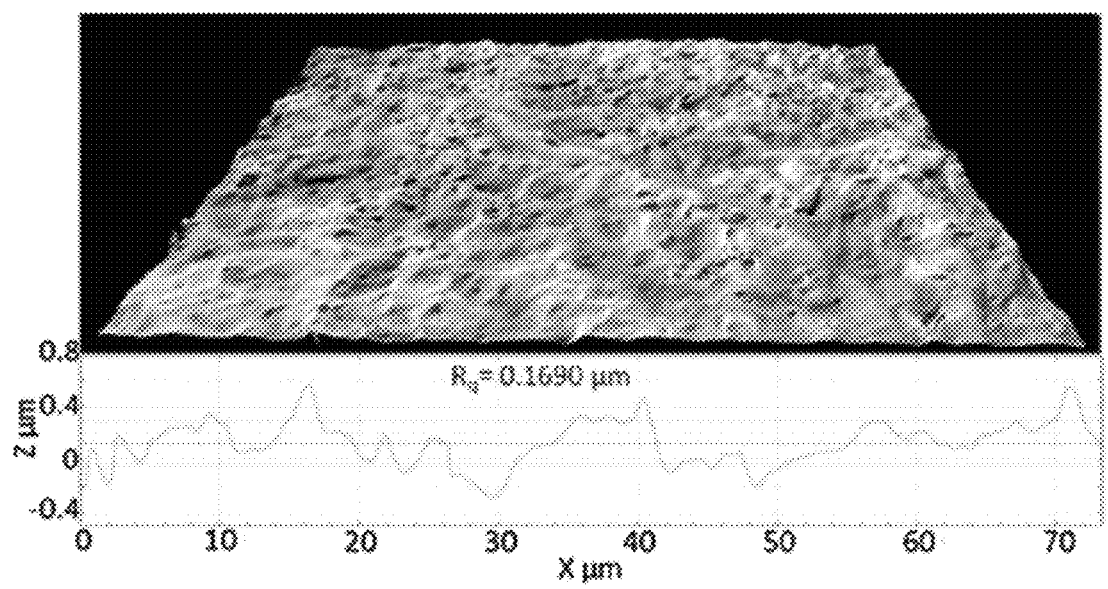
FIGS. 3A-E are images showing topography and surface roughness (Rq) of various waxes: carnauba wax (FIG. 3A); a mixture of C52 polyamide (90.0 wt %) and C38 diamide (10.0 wt %) (FIG. 3B); a mixture of C52 polyamide (80.8 wt %), C38 diamide (10.9 wt %), and C29 R-diamide (8.3 wt %) (FIG. 3C); a mixture of C52 polyamide (71.8 wt %), C38 diamide (11.6 wt %), and C29 R-diamide (16.6 wt %) (FIG. 3D); and a mixture of C52 polyamide (62.9 wt %), C38 diamide (12.4 wt %), and C29 R-diamide (24.7 wt %) (FIG. 3E).
Figure 3B:
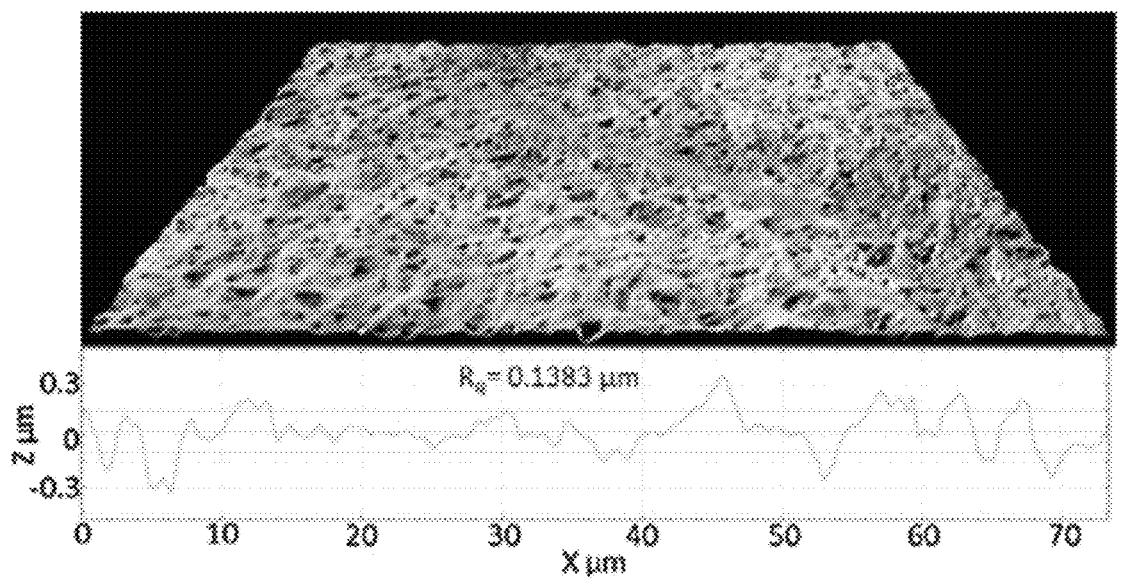
Figure 3C:
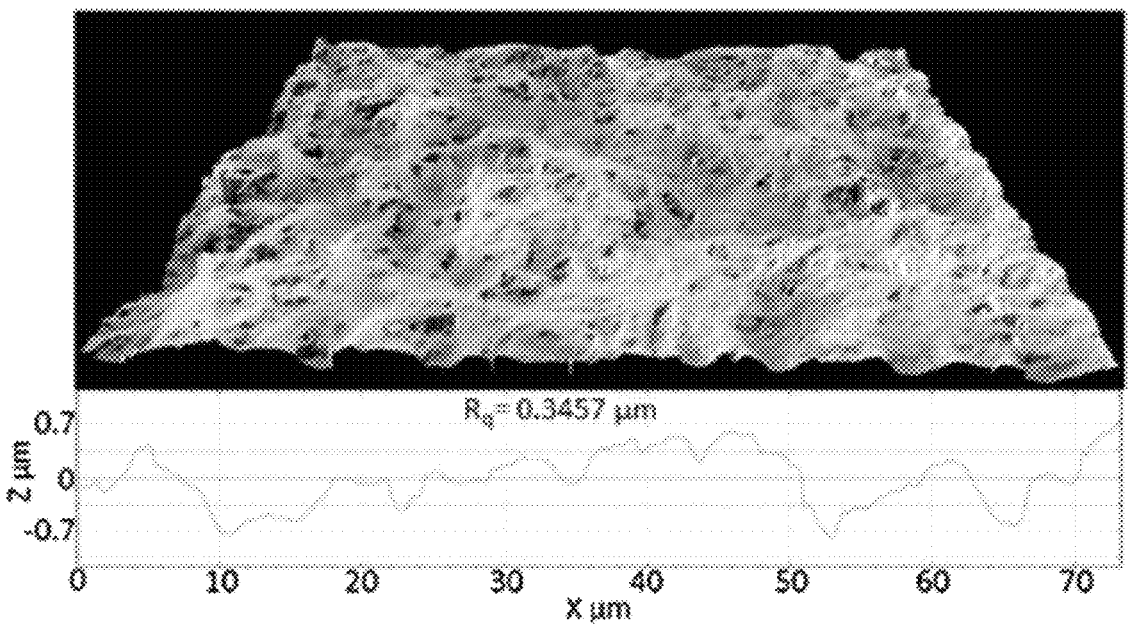
Figure 3D:
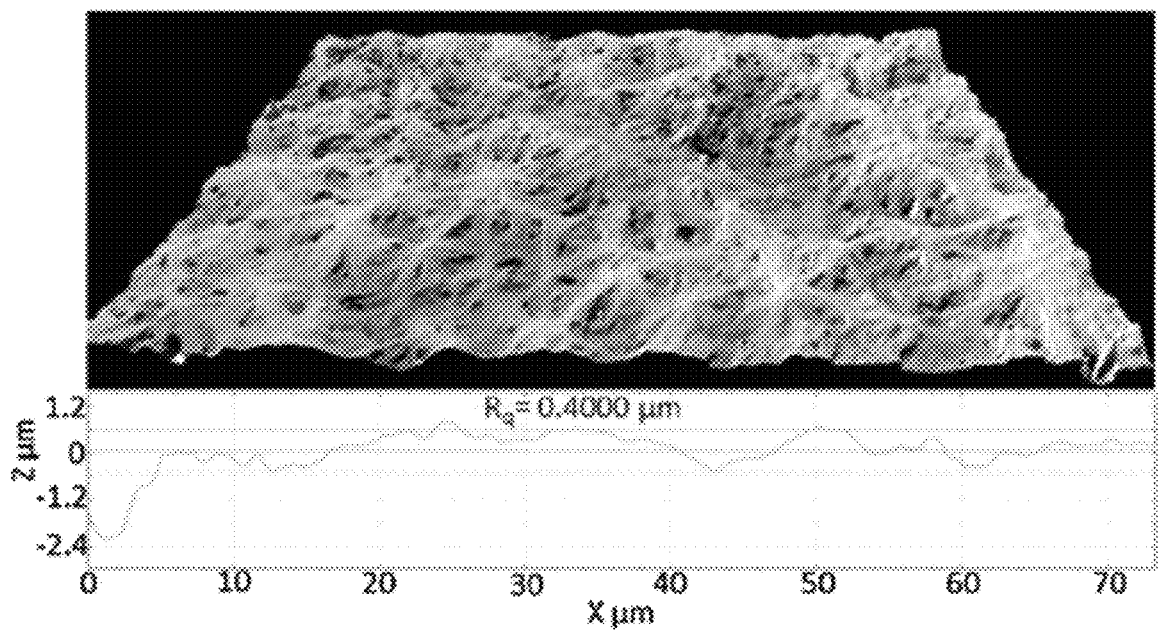
Figure 3E:
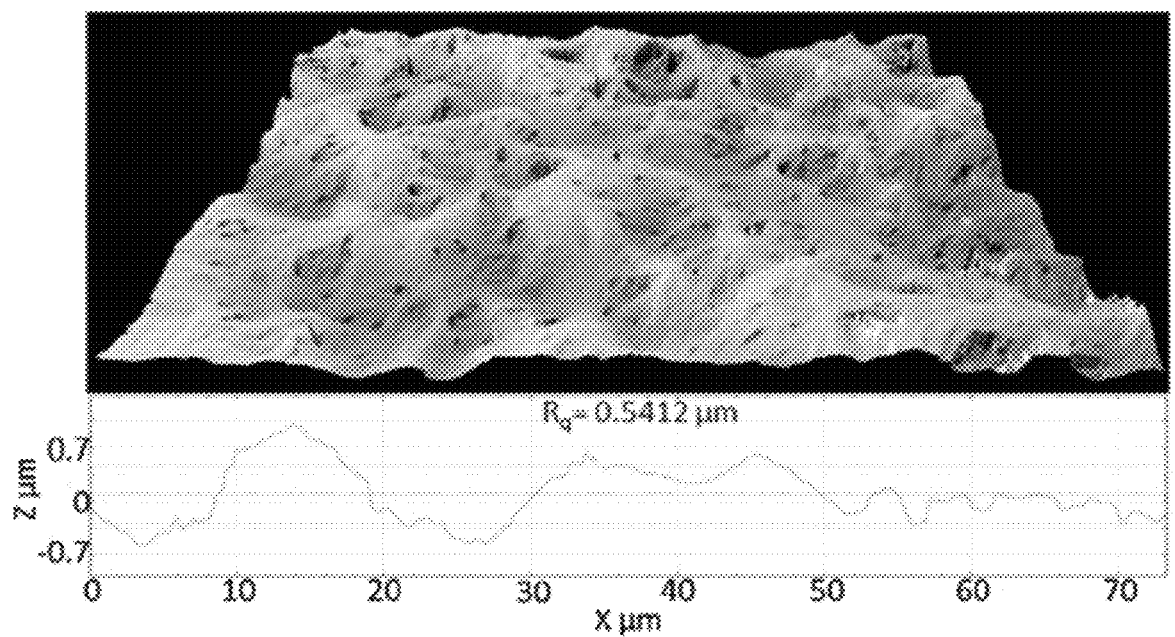

Effect of Chain Length and Functional Groups on Hardness and Surface Properties of the Material Two units of monoamide were linked either by C6 diacid or C12 diacid. Due to the different chain length of the diacid, the subsequent polyamide formed also differed by 6 carbons. FIG. 2 shows that 6 C difference in chain length led to a significant difference in hardness of the diamide. The polyamide formed using C12 diacid has significantly higher hardness than the ones formed with C6 diacid. It was also observed that a higher content of polyamide in the mixture resulted in a higher hardness. Others also have reported that increase of chain length can lead to higher hardness of the waxes, and high hardness is mainly contributed by those compounds with long fatty acyl chain (Yao et al., "Synthesis and Characterization of Acetylated and Stearylyzed Soy Wax," *J. Am. Oil Chem. Soc.* 90:1063-1071 (2013); U.S. Pat. No. 3,129,104 to Callinan et al., which are hereby incorporated by reference in their entirety).

Cinnamic ring was introduced into the structure to evaluate its effect on surface properties. By varying the mixing ratio of mixtures 2̂ and 3̂, waxes with different amounts of cinnamic acid were obtained and the effect of cinnamic ring was quantified. The topography of these waxes was recorded, their surface roughness was determined, and these properties were compared to those of carnauba wax. The topography of waxes changed significantly with the amount of C29 R-diamide (FIGS. 3A-E). The polyamide (90 wt %) and diamide (10 wt %) mixture had a lower surface roughness (Rq of 0.1383 mm) compared to carnauba wax (0.1690 mm). Increasing the content of C29 R-diamide from 0 to 24.7 wt % significantly increased surface roughness from 0.1383 to 0.5412 mm. This is very likely due to the cinnamic ring structure interfering with molecular packing, leading to uneven crystallization that resulted a coarser surface.

To compare the surface friction of different wax samples, AFM trace-retrace curves were obtained (FIGS. 4A-E). A higher surface friction leads to a greater lateral voltage difference between the trace and retrace curves. FIG. 4F shows that all diamide wax samples resulted in smaller lateral voltage differences compared to carnauba wax. Since this voltage difference value is a measure of the surface coefficient of friction (Duong et al., "Surface Roughness and Frictional Coefficient of Hip Implant Using Atomic Force Microscopy," 55th Annual Meeting of the Orthopaedic Research Society, Poster No. 2324 (2009), which is hereby incorporated by reference in its entirety), diamide waxes were shown to have significantly lower surface friction than carnauba wax. The addition of cinnamic ring tended to decrease surface friction. Increasing sample size and measuring a larger areas of surface using traditional tribological means may lead to better evaluations of the friction properties.

Figure 5:
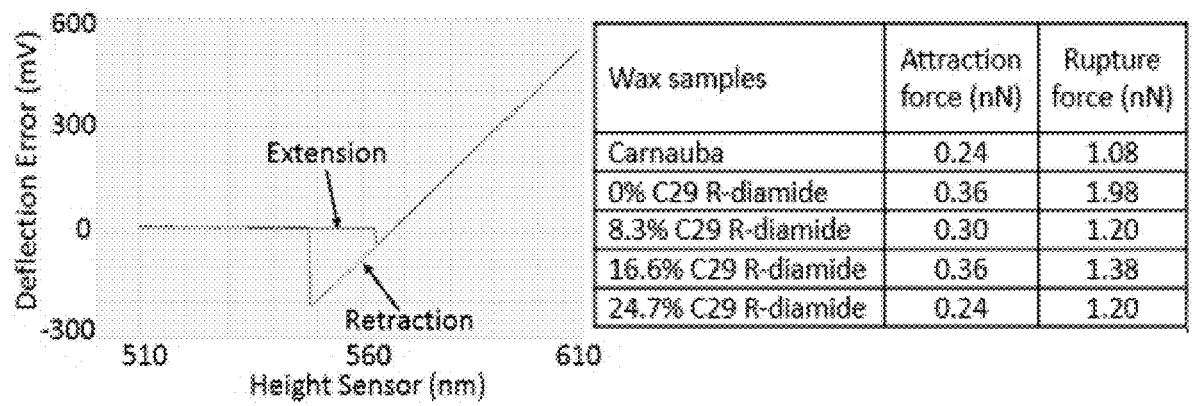
FIG. 5 is an image showing typical AFM extend-retract curve of wax samples (left) and estimated attraction and rupture forces of waxes with different amount of cinnamic ring in comparison with carnauba wax (right).

The AFM extend-retract curves for the wax samples were obtained and an example is shown in FIG. 5. The attraction force of the wax surface to the probe during extension and the rupture force needed to break away from the surface during retraction were determined. The summary table in FIG. 5 shows that the difference in attraction force of all the wax samples was small, however, a larger difference in rupture force was observed. The small difference in attraction forces was probably because the electrons on all the wax samples were discharged using a static discharge device. Carnauba wax had the lowest attraction (0.24 nN) and rupture forces (1.08 nN), while the mixture of polyamide and diamide had the highest (0.36 nN and 1.98 nN). Mixtures with the addition of C29 R-diamide had significantly lowered rupture forces, and this phenomenon corresponded to the falling trend of surface friction found in the trace-retrace AFM mode. Low rupture force which also means low adhesion should be desirable for applications such as car waxing since such a property may lead to dust resistance or easier dust removal.

Figure 6:
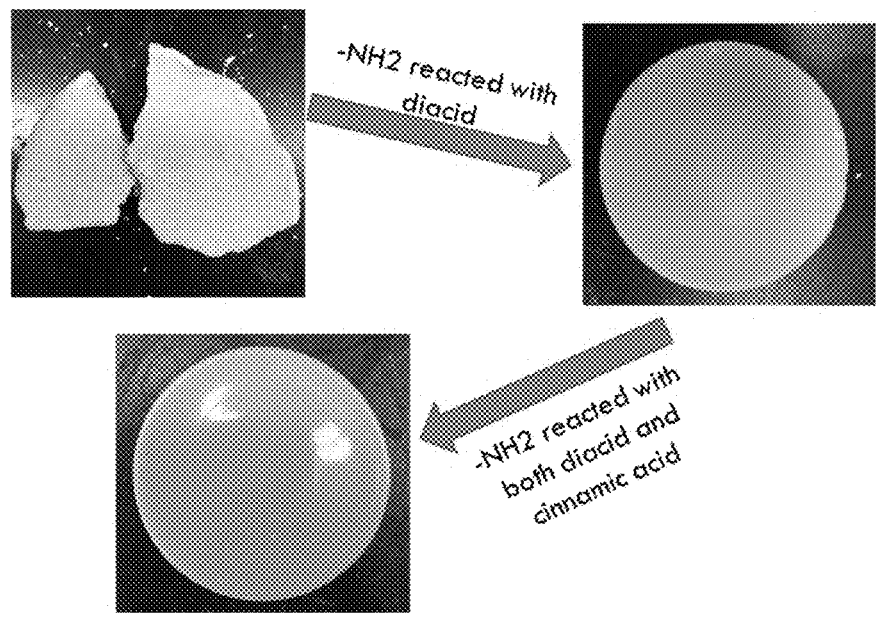
FIG. 6 is an image showing effect of attaching cinnamic ring to the structure (12.4 wt % diamide with cinnamic rings) on surface property.

FIG. 6 shows the surface appearance changes of one of the materials at different reaction stages. Monoamide with a free amine group has a rough and powdery surface. After the free amine group was reacted with a diacid, the material became more uniform and less powdery. When cinnamic ring was incorporated into the system, the resulting materials showed apparent surface shininess. Different percentages of a cinnamic rings lead to different degrees of surface gloss. Table 2 shows that the introduction of a cinnamic ring structure significantly affected surface gloss of the wax. It was observed that gloss of the wax increased as the content of diamide with cinnamic ring increased from 4.3 wt % to 12.4 wt % (corresponding to 5 wt % and 15 wt % of mixture 3̂). However, a further increase of the content to 41.3 wt % (corresponding 50 wt % of mixture 3̂) did not show significant effect on surface gloss. Therefore, 15 wt % of mixture 3̂ and 85 wt % of mixture 2̂ values were selected as the optimal mixing ratio.

TABLE 2

Surface Gloss of Selected Waxes.

| Wax samples | Surface gloss (Gu) |
| --- | --- |
| Carnauba wax | $62.9 \pm 0.4^a$ |
| 100 wt % 2̂ | $28.9 \pm 0.2^d$ |
| 95 wt % 2̂ + 5 wt % 3̂ | $28.3 \pm 1.5^d$ |
| 90 wt % 2̂ + 10 wt % 3̂ | $27.1 \pm 1.2^d$ |
| 85 wt % 2̂ + 15 wt % 3̂ | $42.2 \pm 2.8^b$ |
| 80 wt % 2̂ + 20 wt % 3̂ | $39.1 \pm 1.8^c$ |
| 70 wt % 2̂ + 30 wt % 3̂ | $27.0 \pm 2.1^d$ |
| 50 wt % 2̂ + 50 wt % 3̂ | $20.9 \pm 1.3^e$ |

Means followed by the same superscript are not significantly different, $\rho > 0.05$.

A literature survey indicated that very few previous studies have directly related the cinnamic ring content to the shininess and smoothness of carnauba wax. However, many suspected that this structure could be responsible for the desirable surface properties of carnauba wax (Vandenburg et al., "Aromatic Acids of Carnauba Wax," *J. Am. Oil Chem.* 44:659-662 (1967); Mohamed et al., "Isolation of a Cinnamic Acid-Metabolizing *Clostridium Glycolicum* Strain From Oil Mill Wastewaters and Emendation of the Species Description," *Int. J. Syst. Evol. Microbiol.* 51:2049-2054 (2001), which are hereby incorporated by reference in their entirety). The mechanism of the ring structure improving gloss and lowering surface friction and rupture force is not well understood at this time. A comprehensive theoretical study on such structure-function relationship is necessary.

Figure 7:
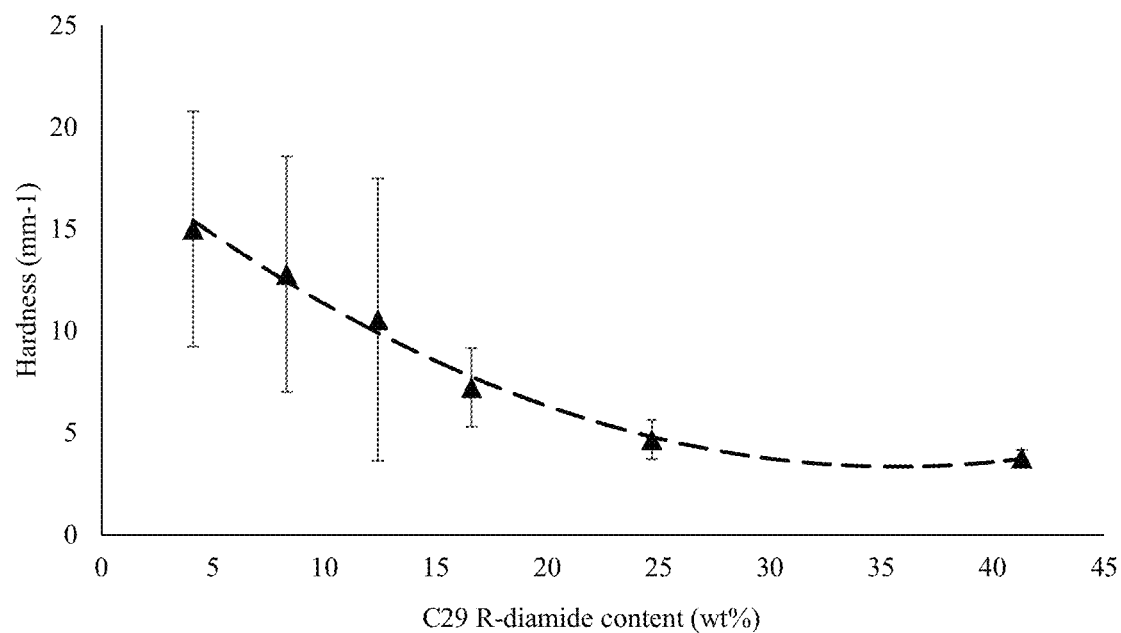
FIG. 7 is a graph showing effect of introducing cinnamic ring structure on hardness of the material.

Although introducing the cinnamic ring may be beneficial for surface properties, it negatively affected hardness of the material. FIG. 7 shows the hardness decreased greatly when the content of C29 R-diamide increased. When 12.4 wt % of the C29 R-diamide was mixed in the system, the hardness of the material was still comparable to carnauba. However, further increasing the content to 41.3 wt % significantly decreased hardness so that it became only ⅓ of carnauba hardness.

Figure 8:
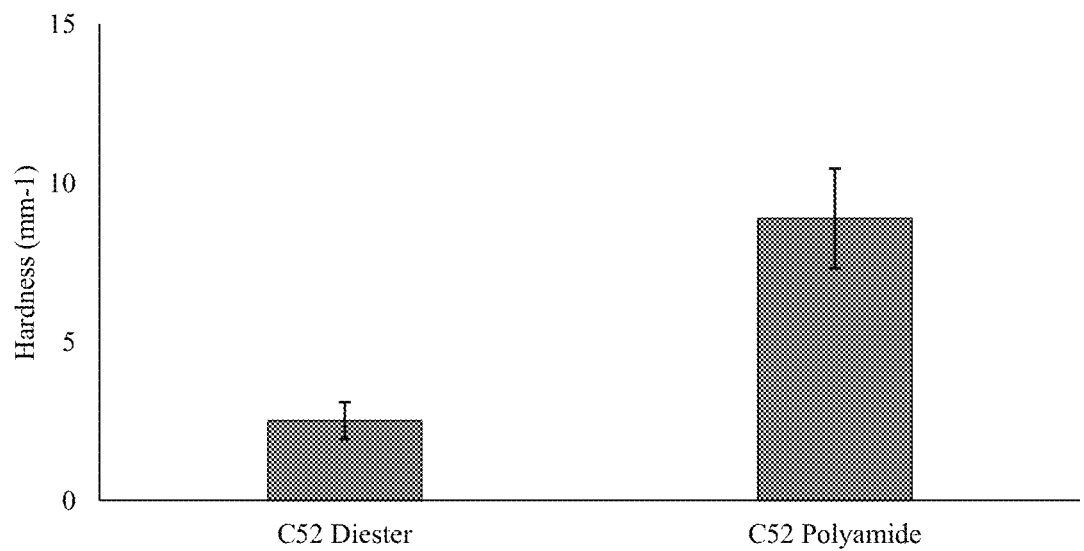
FIG. 8 is the graph showing comparison of hardness of long chain diester and diamide.

In order to illustrate the important function that the amide bond offers, a long chain diester (52 carbon atoms) which has the same carbon number as the polyamide (52 carbon atoms) was also synthesized. The hardness and melting temperature of the diester and diamide were compared and shown in FIG. 8. The polyamide has significantly higher hardness (8.9 mm$^{-1}$) and melting temperature (150° C.) compared to the diester's hardness (2.5 mm$^{-1}$) and melting temperature (77° C.). This is probably because the —NH group and O═C group of the polyamide can engage in hydrogen bonding. Such hydrogen bonding improves molecular packing, thereby increasing hardness and melting point. By contrast, in the long chain diesters, there is no such hydrogen bonding.

Figure 9:
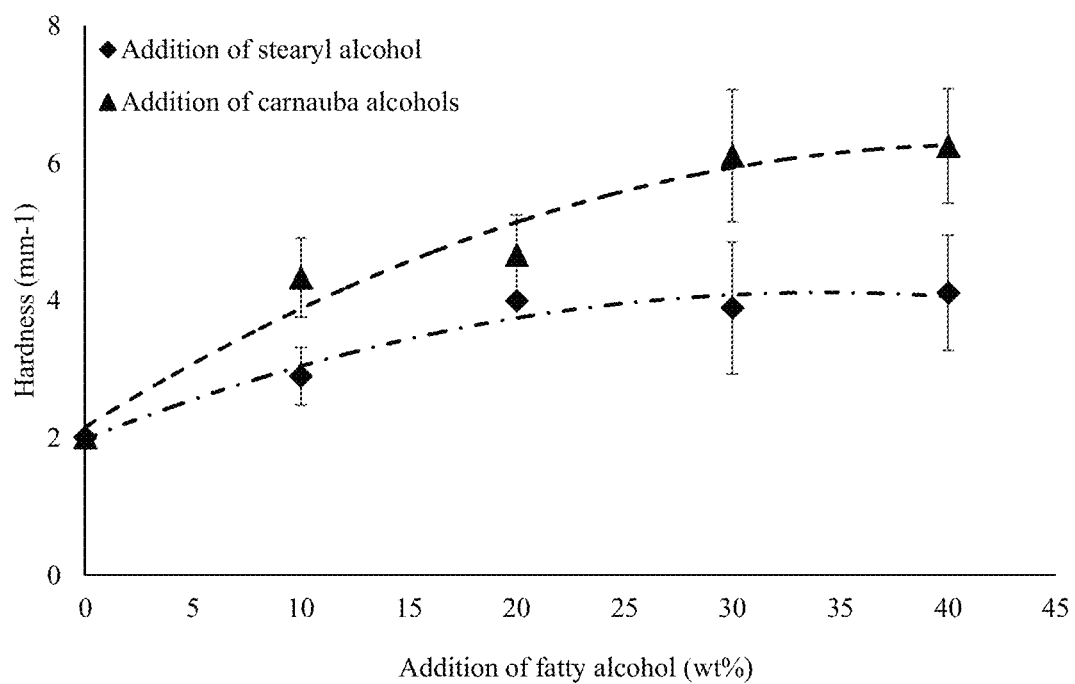
FIG. 9 is a graph showing the effect of fatty alcohol content in a diester on wax hardness.

Long-chain fatty alcohols (C28-C34) obtained from carnauba wax were used to evaluate the effect of fatty alcohols on hardness of C52 diester. Stearyl alcohol was used as a comparison. FIG. 9 shows that the hardness of the resulting mixture increased with the content of stearyl alcohol and carnauba alcohols. However, the hardness of the mixture eventually plateaued and none of the mixtures had a hardness comparable to carnauba wax. The increase in hardness is very likely due to the fatty alcohol's hydroxyl groups being able to hydrogen bond between themselves and with the esters. Such interaction can lead to a more rigid packing and higher hardness. Carnauba alcohols resulted in a higher hardness than stearyl alcohol did due to their longer chain fatty alcohols. Carnauba alcohols had higher hardness (4.6 mm$^{-1}$) than stearyl alcohol (1.7 mm$^{-1}$) when measured alone.

The feasibility of directly using FHSO instead of SFFA to synthesize polyamide was also tested. The material produced did not have the desirable properties that carnauba wax has. The melting point of the material is high (i.e. 120° C.), but the hardness (2.77±0.31 mm$^{-1}$) was only about one-third that of carnauba wax (9.05±1.62 mm$^{-1}$) and the SFFA derived (8.57±1.78 mm$^{-1}$) substitute. The material also has an undesirably rough surface and powdery texture. This may have been caused by mono/diglycerides interfering with hydrogen bonding between —NH and O=C, leading to a less orderly packing, and resulting in lower hardness and poor texture properties. The residue of mono/diglycerides may also interfere with the reaction of the monoamide with a free amine group and cinnamic acid and possibly leads to cinnamoyl glycerol (Holser et al., "Preparation and Characterization of 4-Methoxyl Cinnamoyl Glycerol," *J. Am. Oil Chem. Soc.* 85: 347-351 (2008), which is hereby incorporated by reference in its entirety) which lowers the hardness and melting point.

Melting Properties of the Waxes Synthesized

The melting points of all materials were determined by DSC. Two peaks were observed for all materials formed in reaction 1. One peak at about 80° C. represents the melting point of the monoamide with free amine group, and the other peak at about 110° C. represents the melting point of the short chain diamide (38 carbon). After the free amine group in the monoamide was reacted with diacids, all materials became similar in their melting peaks (145-150° C.). With 12.4 wt % of diamide having a cinnamic ring structure, a material (DR-wax) that is comparable to carnauba wax was obtained. The physical properties of the material (76.3 wt % polyamide with 52 carbon atoms, 11.3 wt % short chain diamide with 38 carbon atoms, and 12.4 wt % diamide of 29 carbon atoms having cinnamic ring attached) are compared to carnauba wax and shown in Table 3.

TABLE 3

Physical Properties of DR Wax in Comparison to Carnauba Wax.

| Property | DR-Wax | Carnauba wax |
|---|---|---|
| Appearance | hard solid | hard solid |
| Color | dark yellow to brown | yellow to brown |
| Melting point | 145-150° C. | 81-86° C. |
| Needle penetration (ASTM D1321) | 0.12 mm (8.57 mm$^{-1}$) | 0.11 mm (9.05 mm$^{-1}$) |
| Water contact angle | ~65° | ~45° |

DR-wax: a mixture of 76.3 wt % C52 polyamide, 11.3 wt % C38 diamide, and 12.4 wt % C29 R-diamide.

CONCLUSION

With excess ETD present with saturated fatty acids, monoamides with a free amine group can be formed. The reaction of the free amine group with a diacid resulted in a material with high hardness, high melting point, and improved matrix uniformity. Incorporation of diamide with cinnamic ring structure contributed to a visibly smoother and shinier surface of the product, a tremendously improved surface characteristic. A wax containing 76.3 wt % of polyamide with 52 carbon atoms, 11.3 wt % of short chain diamide with 38 carbon atoms, and 12.4 wt % of diamide of 29 carbon atoms having cinnamic ring attached showed optimal physical properties that are comparable to those of carnauba wax.

A wax material containing polyamide, diamide, and diamide having a cinnamic ring structure was successfully synthesized and demonstrated to have a set of physical properties comparable to those of carnauba wax, except the much higher melting temperature. It has been difficult to create a wax material having similar hardness as carnauba wax has, and this work demonstrates how this can be done. This material should find applications where high temperature resistance is needed. The structure-function relationship discussed should provide insights for future explorations of using biorenewable resources and feedstocks to mimic natural materials for their desirable properties.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A fatty acid amide compound having the Formula (I):

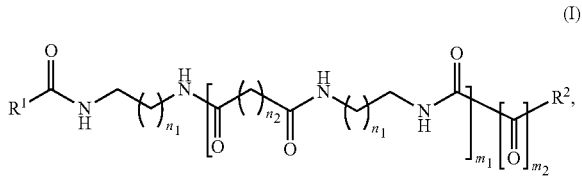

wherein:
R$^1$ is a substituted or unsubstituted C$_3$ to C$_{50}$ alkyl or substituted or unsubstituted aryl;
R$^2$ is H, substituted or unsubstituted C$_3$ to C$_{50}$ alkyl, substituted or unsubstituted arylalkyl, substituted or unsubstituted arylalkenyl, or substituted or unsubstituted aryl;
n$_1$ is an integer from 1 to 10;
n$_2$ is an integer from 1 to 20;
m$_1$ is 0 or 1; and
m$_2$ is 0 or 1, and
wherein m$_1$+m$_2$ cannot be 2,
wherein if R$^1$ is a substituted C$_3$ to C$_{50}$ alkyl, then R$^2$ is H, unsubstituted C$_3$ to C$_{50}$ alkyl, substituted or unsubstituted arylalkyl, substituted or unsubstituted arylalkenyl, substituted or unsubstituted aryl, or C$_3$ to C$_{50}$ alkyl substituted with alkyl, halogen, haloalkyl, hydroxy, lower alkoxy, carboxy, carbalkoxy, carboxamido, cyano, carbonyl, nitro, amino, alkylamino, dialkylamino, mercapto, alkylthio, sulfoxide, sulfone, acylamino, amidino, phenyl, benzyl, heteroaryl, phenoxy, benzyloxy, or heteroaryloxy; or wherein if $R^2$ is a substituted $C_3$ to $C_{50}$ alkyl, then $R^1$ is an unsubstituted $C_3$ to $C_{50}$ alkyl, substituted or unsubstituted aryl, or $C_3$ to $C_{50}$ alkyl substituted with alkyl, halogen, haloalkyl, hydroxy, lower alkoxy, carboxy, carboalkoxy, carboxamido, cyano, carbonyl, nitro, amino, alkylamino, dialkylamino, mercapto, alkylthio, sulfoxide, sulfone, acylamino, amidino, phenyl, benzyl, heteroaryl, phenoxy, benzyloxy, or heteroaryloxy.

2. The fatty acid amide compound of claim 1, wherein $m_1$ is 0; $m_2$ is 0; and $R^2$ is H.

3. The fatty acid amide compound of claim 1, wherein $m_1$ is 0; $m_2$ is 1; and $R^2$ is a substituted or unsubstituted $C_3$ to $C_{50}$ alkyl, substituted or unsubstituted arylalkyl, or substituted or unsubstituted arylalkenyl.

4. The fatty acid amide compound of claim 1, wherein $m_1$ is 1; $m_2$ is 0; and $R^2$ is a substituted or unsubstituted $C_3$ to $C_{50}$ alkyl.

5. The fatty acid amide compound of claim 1, wherein $n_2$ is an integer from 6 to 12.

6. A wax composition comprising a plurality of fatty acid amide compounds having the Formula (I):

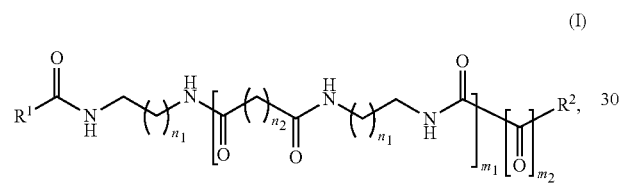

(I)

wherein:

$R^1$ a substituted or unsubstituted $C_3$ to $C_{50}$ alkyl or substituted or unsubstituted aryl;

$R^2$ is H, substituted or unsubstituted $C_3$ to $C_{50}$ alkyl, substituted or unsubstituted arylalkyl, substituted or unsubstituted arylalkenyl, or substituted or unsubstituted aryl;

$n_1$ is an integer from 1 to 10;

$n_2$ is an integer from 1 to 20;

$m_1$ is 0 or 1; and $m_2$ is 0 or 1, and wherein $m_1+m_2$ cannot be 2, wherein if $R^1$ is a substituted $C_3$ to $C_{50}$ alkyl, then $R^2$ is H, unsubstituted $C_3$ to $C_{50}$ alkyl, substituted or unsubstituted arylalkyl, substituted or unsubstituted arylalkenyl, substituted or unsubstituted aryl, or $C_3$ to $C_{50}$ alkyl substituted with alkyl, halogen, haloalkyl, hydroxy, lower alkoxy, carboxy, carboalkoxy, carboxamido, cyano, carbonyl, nitro, amino, alkylamino, dialkylamino, mercapto, alkylthio, sulfoxide, sulfone, acylamino, amidino, phenyl, benzyl, heteroaryl, phenoxy, benzyloxy, or heteroaryloxy; or wherein if $R^2$ is a substituted $C_3$ to $C_{50}$ alkyl, then $R^1$ is an unsubstituted $C_3$ to $C_{50}$ alkyl, substituted or unsubstituted aryl, or $C_3$ to $C_{50}$ alkyl substituted with alkyl, halogen, haloalkyl, hydroxy, lower alkoxy, carboxy, carboalkoxy, carboxamido, cyano, carbonyl, nitro, amino, alkylamino, dialkylamino, mercapto, alkylthio, sulfoxide, sulfone, acylamino, amidino, phenyl, benzyl, heteroaryl, phenoxy, benzyloxy, or heteroaryloxy.

7. The wax composition of claim 6, wherein the wax composition comprises compounds of Formula (I) wherein $m_1$ is 0; $m_2$ is 0; and $R^2$ is H.

8. The wax composition of claim 6, wherein the wax composition comprises compounds of Formula (I) wherein $m_1$ is 0; $m_2$ is 1; and $R^2$ is a substituted or unsubstituted $C_3$ to $C_{50}$ alkyl, substituted or unsubstituted arylalkyl, or substituted or unsubstituted arylalkenyl.

9. The wax composition of claim 6, wherein the wax composition comprises compounds of Formula (I) wherein $m_1$ is 1; $m_2$ is 0; and $R^2$ is a substituted or unsubstituted $C_3$ to $C_{50}$ alkyl.

10. The wax composition of claim 6, wherein the wax composition comprises compounds of Formula (I) wherein $n_2$ is an integer from 6 to 12.

11. The wax composition of claim 6, wherein the wax composition has a melting point ranging from 50° C. to 200° C.

12. The wax composition of claim 6, wherein the wax composition has a penetration hardness of 3.0 mm or below, measured by a standard needle penetration test according to the ASTM D1321 standard, with a 100 g cone and the penetration being conducted for 5 seconds at 23° C.

13. The wax composition of claim 6, further comprising one or more natural waxes.

14. A coated material comprising:

a substrate and the wax composition of claim 6 coated on said substrate.

15. A process for preparing a compound of Formula (I):

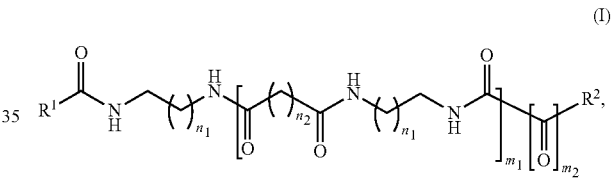

(I)

said process comprising:

providing one or more monoamide compounds having the Formula (IV):

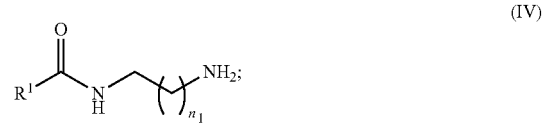

(IV)

providing one or more acids having the Formula (Va) or Formula (Vb)

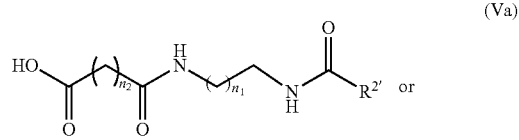

(Va)

(Vb)

wherein
- $R^1$ is a substituted or unsubstituted $C_3$ to $C_{50}$ alkyl;
- $R^2$ is substituted or unsubstituted $C_3$ to $C_{50}$ alkyl, substituted or unsubstituted arylalkyl, substituted or unsubstituted arylalkenyl, or substituted or unsubstituted aryl;
- $R^{2'}$ is substituted or unsubstituted $C_3$ to $C_{50}$ alkyl, substituted or unsubstituted arylalkyl, substituted or unsubstituted arylalkenyl, or substituted or unsubstituted aryl;
- $n_1$ is an integer from 1 to 10;
- $n_2$ is an integer from 1 to 20;
- $m_1$ is 0 or 1; and
- $m_2$ is 0 or 1,
wherein $m_1+m_2$ cannot be 2, and
reacting the one or more monoamide compounds having the Formula (IV) with the one or more acids having Formula (Va) or Formula (Vb) under conditions effective to make the compound of Formula (I).

* * * * *